US012601909B2

(12) United States Patent     (10) Patent No.:    US 12,601,909 B2

Kumar Agrawal et al.       (45) Date of Patent:     Apr. 14, 2026

(54) ELECTRONIC DEVICES AND CORRESPONDING METHODS FOR RENDERING CONTENT FOR A COMPANION DEVICE

(71) Applicant: Motorola Mobility LLC, Chicago, IL (US)

(72) Inventors: Amit Kumar Agrawal, Bangalore (IN); Igor Kovalenko, Palatine, IL (US)

(73) Assignee: Motorola Mobility LLC, Chicago, IL (US)

( * ) Notice: Subject to any disclaimer, the term of this patent is extended or adjusted under 35 U.S.C. 154(b) by 346 days.

(21) Appl. No.: 18/244,808

(22) Filed: Sep. 11, 2023

(65) Prior Publication Data

US 2025/0085532 A1     Mar. 13, 2025

(51) Int. Cl.
     *G02B 27/00*      (2006.01)
     *A61B 3/00*      (2006.01)
     *G02B 27/01*      (2006.01)

(52) U.S. Cl.
     CPC ........ *G02B 27/0025* (2013.01); *A61B 3/0041* (2013.01); *G02B 27/0093* (2013.01); *G02B 27/0172* (2013.01); *G02B 2027/0123* (2013.01); *G02B 2027/0178* (2013.01)

(58) Field of Classification Search
None
See application file for complete search history.

(56) References Cited

U.S. PATENT DOCUMENTS 12,002,435 B1     6/2024   Kumar Agrawal et al.

OTHER PUBLICATIONS

Kovalenko, et al., "Electronic Devices and Corresponding Methods for Delivering an Extended Display Identification (EDID) Extension Identifying Interpupillary Distance Metrics", Application As Filed Apr. 24, 2023; U.S. Appl. No. 18/138,169.

*Primary Examiner* — Aneeta Yodichkas

(74) *Attorney, Agent, or Firm* — Philip H. Burrus, IV

(57)        ABSTRACT

An electronic device includes a wireless communication device, a non-transient memory device, and one or more processors operable with the wireless communication device and the non-transient memory device. The one or more processors identify a companion device electronically in communication with the wireless communication device as being a wearable glass projection device when a received extended display identification (EDID) extension(s) from the companion device include a non-zero field of view, pixel density, and/or interpupillary distance value. The one or more processors can render content for the wearable glass projection device as a function of the non-zero field of view, pixel density, and/or interpupillary distance value, and can optionally apply a rendering adjustment to the content as a function of optical data associated with a user of the electronic device stored in the non-transient memory device.

20 Claims, 9 Drawing Sheets

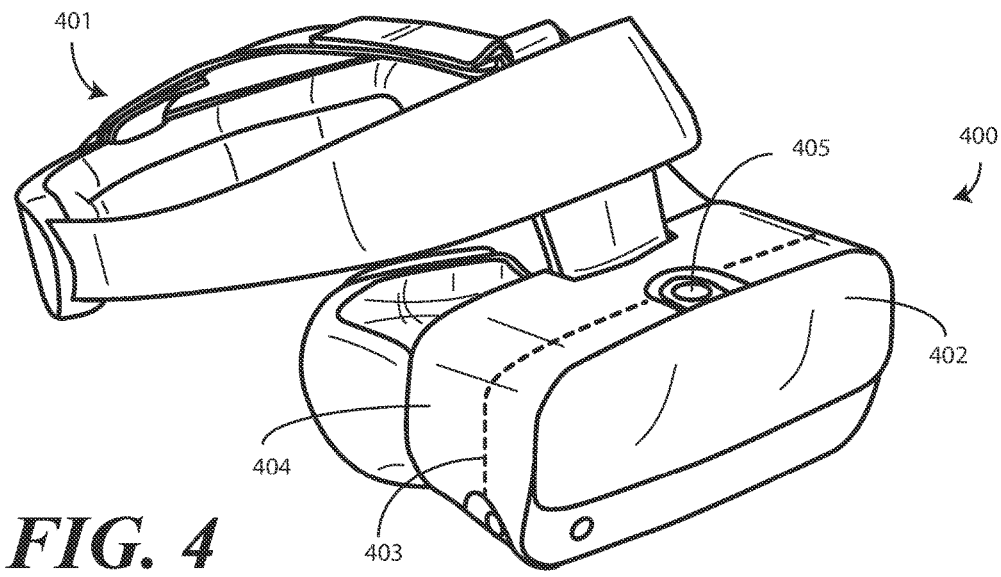

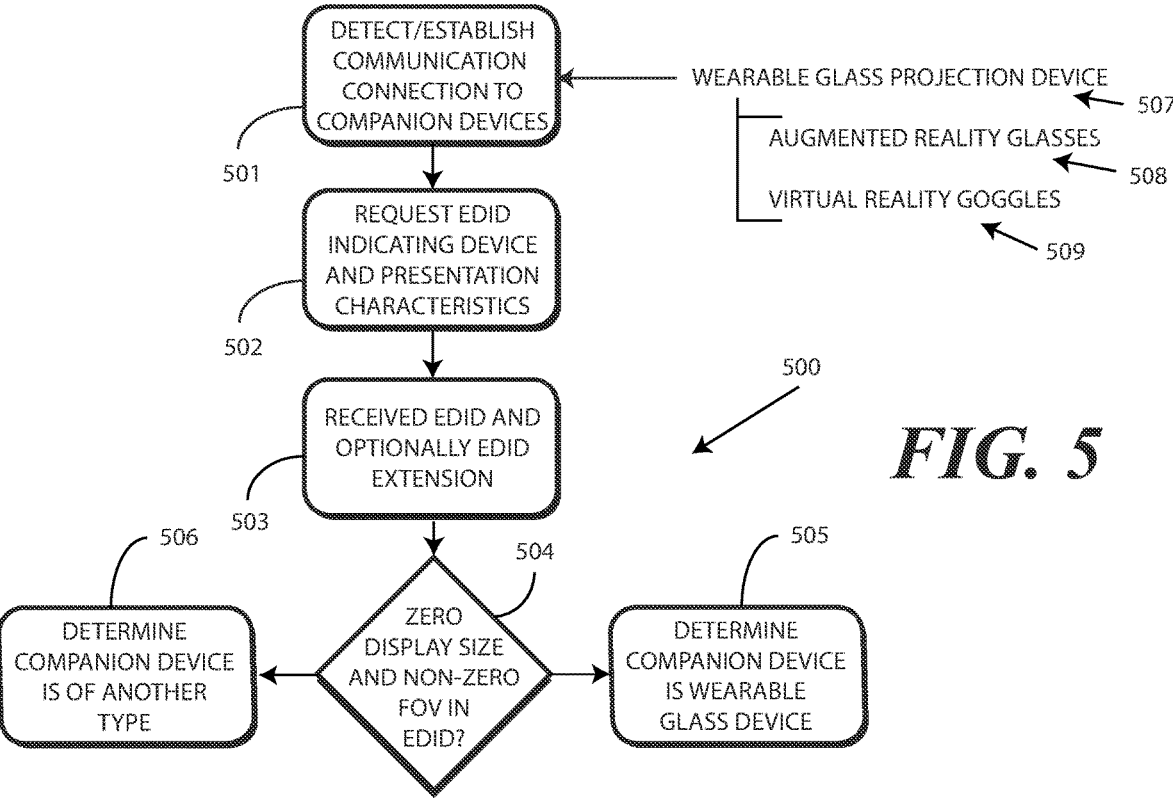

DETECT/ESTABLISH COMMUNICATION CONNECTION TO COMPANION DEVICES

501

WEARABLE GLASS PROJECTION DEVICE — 507

AUGMENTED REALITY GLASSES — 508

VIRTUAL REALITY GOGGLES — 509

REQUEST EDID INDICATING DEVICE AND PRESENTATION CHARACTERISTICS

502

RECEIVED EDID AND OPTIONALLY EDID EXTENSION

DETERMINE COMPANION DEVICE IS OF ANOTHER TYPE

ZERO DISPLAY SIZE AND NON-ZERO FOV IN EDID?

504

DETERMINE COMPANION DEVICE IS WEARABLE GLASS DEVICE

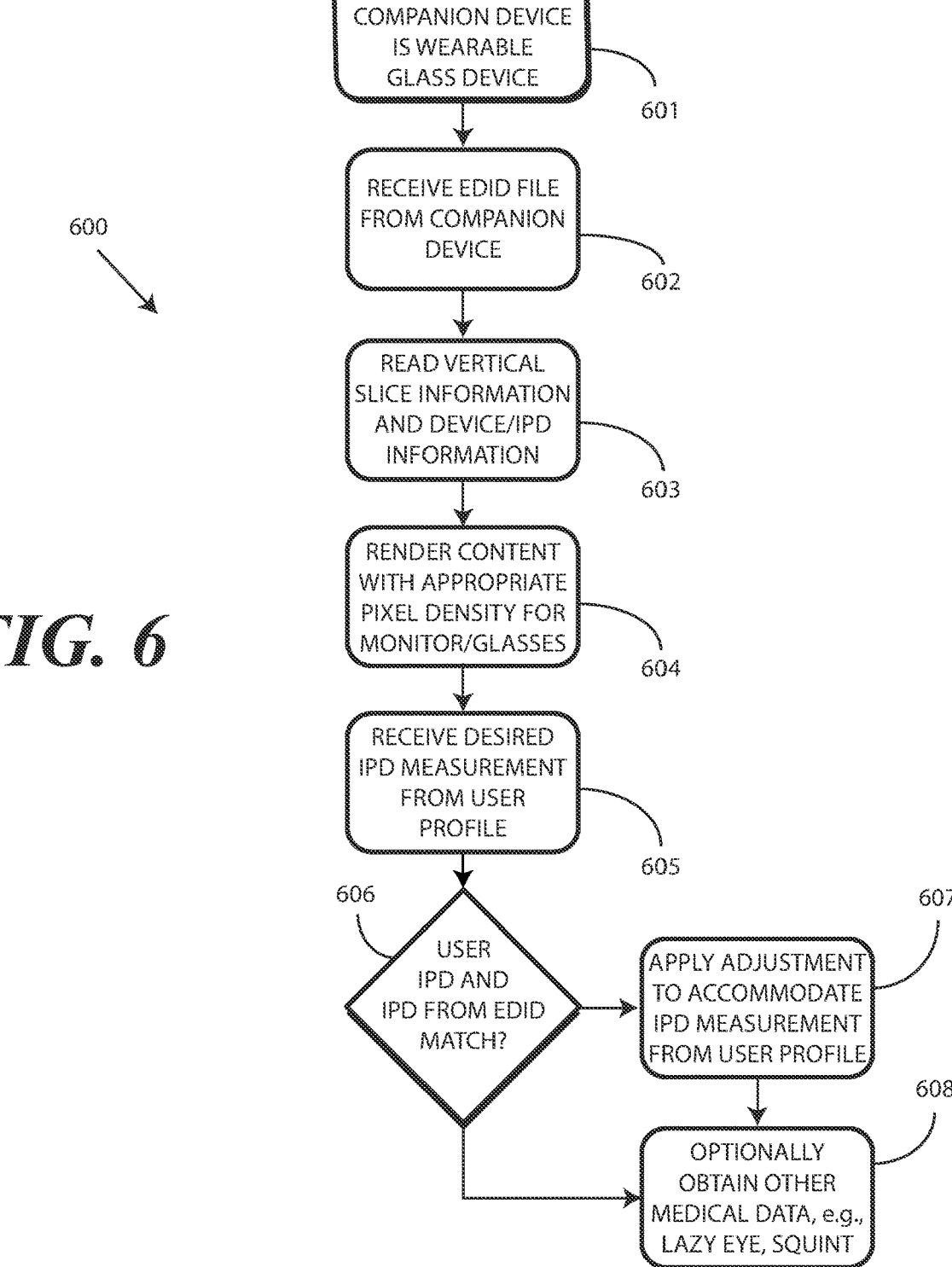

DETERMINE COMPANION DEVICE IS WEARABLE GLASS DEVICE
601

RECEIVE EDID FILE FROM COMPANION DEVICE
602

READ VERTICAL SLICE INFORMATION AND DEVICE/IPD INFORMATION
603

RENDER CONTENT WITH APPROPRIATE PIXEL DENSITY FOR MONITOR/GLASSES
604

RECEIVE DESIRED IPD MEASUREMENT FROM USER PROFILE
605

606
USER IPD AND IPD FROM EDID MATCH?

607
APPLY ADJUSTMENT TO ACCOMMODATE IPD MEASUREMENT FROM USER PROFILE

608
OPTIONALLY OBTAIN OTHER MEDICAL DATA, e.g., LAZY EYE, SQUINT

609
APPLY OTHER ADJUSTMENTS FOR LAZY EYE, SQUINT, ETC.

610
DELIVER CONTENT TO WEARABLE GLASS PROJECTION DEVICE

| ADDRESS | DATA | GENERAL DESCRIPTION |
|---|---|---|
| 0-7 | Header | Constant Fixed Pattern |
| 8-9<br>10-11<br>12-14<br>16-17 | Manufacturer ID<br>Product ID Code<br>Serial Number<br>Manufacture Date | Display Product<br>Identification |
| 18<br>19 | EDID Version No.<br>EDID Revision No. | EDID Version<br>Information |
| 20<br>21<br>22<br>23<br>24 | Video Input Type<br>Horizontal Size (cm)<br>Vertical Size (cm)<br>Display Gamma<br>Supported Features          802 | Basic display parameters.<br>Video input type, display<br>size, power management,<br>sync, color space, timing<br>capabilities and preferences. |
| 25-34 | Color Characteristicis | Color space<br>Definition |
| 35-36<br>37<br>38-53<br>54-71<br>72-89<br>90-107<br>108-125 | Established Supported Timings<br>Manufacturer's Reserved Timing<br>EDOD Standard Timings Supported<br>Detailed Timing Descriptior Block 1<br>Detailed Timing Descriptor Block 2<br>Detailed Timing Descriptor Block 3<br>Detailed Timing Descriptor Block 4 | Timing information for<br>all resolutions supported<br>by the display. |
| 126 | Extension Flag | Number of optional<br>extension blocks |
| 127 | Checksum | |

*-- PRIOR ART --*

| ADDRESS | GENERAL DESCRIPTION |
|---|---|
| 0 | Always "N," where N is the new extension |
| 1 | Revision number |
| 2 | Pointer to timing descriptors |
| 3 | Number of timing descriptors |
| 4 to d-1 | Data block description indicating field of view and/or pixel density per degree for companion device (zero unless companion device is glasses) |
| d to d+17 | First 18-byte detailed timing descriptor |
| | ⋮ |
| d+18(n-1) to d+18n-1 | Final 18-byte detailed timing descriptor |
| d+18n to 126 | "0" Padding |
| 127 | Checksum |

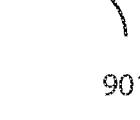

901

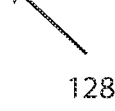

| ADDRESS | GENERAL DESCRIPTION |
|---|---|
| 0 | Always "N," where N is the new extension |
| 1 | Revision number |
| 2 | Pointer to timing descriptors |
| 3 | Number of timing descriptors |
| 4 to d-1 | Data block description indicating user IPD, lazy eye, squint, etc. for companion device (can be represented as a distance or alternatively as default +/- per eye adjustment) |
| d to d+17 | First 18-byte detailed timing descriptor |
| | ⋮ |
| d+18(n-1) to d+18n-1 | Final 18-byte detailed timing descriptor |
| d+18n to 126 | "0" Padding |
| 127 | Checksum |

ELECTRONIC DEVICES AND CORRESPONDING METHODS FOR RENDERING CONTENT FOR A COMPANION DEVICE

BACKGROUND

Technical Field

This disclosure relates generally to electronic devices having communication circuits, and more particularly to electronic devices engaged in the transmission of signals supplied in digital form, including data transmission and telegraphic communication, with a content presentation companion device.

Background Art

The advanced processing power available in modern electronic communication devices, examples of which include smartphones, tablet computers, and laptop computers, enable voice and video communications between people. Additionally, such devices can also engage in videoconferences, stream content such as movies, videos, and television shows, play music, and offer other forms of entertainment. In addition to being tools for communicating with friends, family, and work colleagues, these devices are also real-time multimedia content entertainment devices.

Some electronic devices are equipped to operate in conjunction with companion devices. Illustrating by example, content can be redirected to a content presentation companion device for enhanced visibility and/or provide a user interface to interactively work with content being presented by the electronic device or the companion device. Companion device operability can redirect content from a first device, such as a smartphone, to a second device, such as a monitor, to make events such as movies, television shows, and videoconferences easier to see. It can also allow the companion device to serve as the primary user interface and/or display for the electronic device itself. While a neat feature, configuring operation between an electronic device and different types of companion devices can be cumbersome. It would be advantageous to have electronic devices and systems that make this process simpler.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present disclosure.

FIG. 4 illustrates another explanatory companion device in accordance with one or more embodiments of the disclosure.

FIG. 5 illustrates another explanatory method in accordance with one or more embodiments of the disclosure.

FIG. 6 illustrates still another explanatory method in accordance with one or more embodiments of the disclosure.

FIG. 8 illustrates a prior art extended display identification data (EDID) file structure.

FIG. 9 illustrates one explanatory EDID extension block of data in accordance with one or more embodiments of the disclosure.

FIG. 10 illustrates another explanatory EDID extension block of data in accordance with one or more embodiments of the disclosure.

Figure 1:
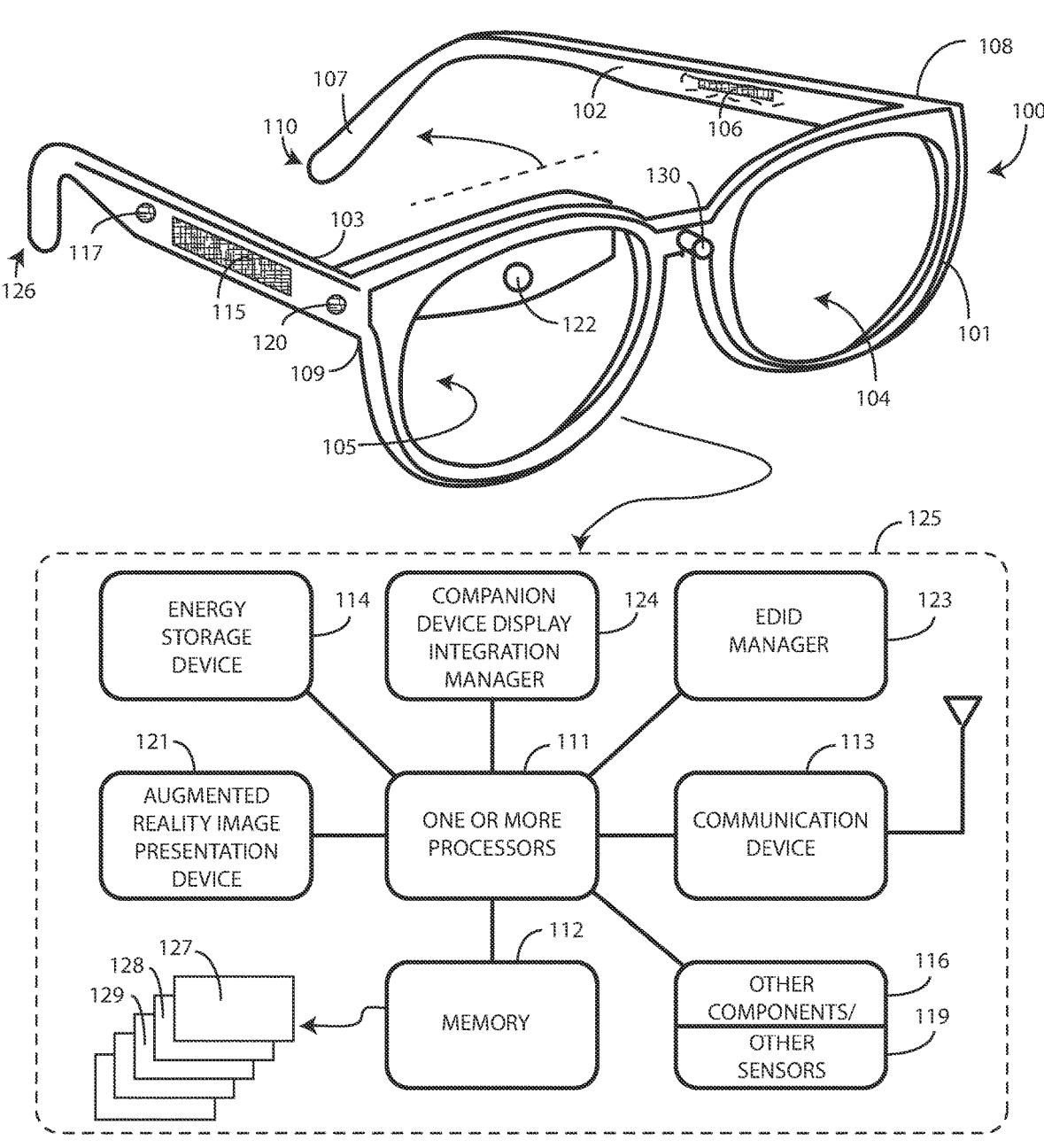
FIG. 1 illustrates one explanatory companion device in accordance with one or more embodiments of the disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

DETAILED DESCRIPTION OF THE DRAWINGS

Before describing in detail embodiments that are in accordance with the present disclosure, it should be observed that the embodiments reside primarily in combinations of method steps and apparatus components related to causing, in response to a communication device detecting establishment of an electrical communication channel with a companion device, the communication device to query the companion device to determine what type of companion device the companion device is and, when the companion device is a wearable glass projection device, obtain slice assignments for each lens of the wearable glass projection device from one or more extensions of extended display identification data (EDID), and render content in accordance with those slice assignments. Illustrating by example, when the wearable glass projection device is an augmented reality device or a virtual reality device, one or more processors of the electronic device can obtain one or more of an interpupillary distance, a pixel density, and/or a field of view from the EDID in addition to the slice assignments and can render the content in accordance with the slice assignments and the one or more of the field of view, the pixel density, and the interpupillary distance. Thereafter, the one or more processors can cause the communication device to transmit the rendered content to the wearable glass projection device.

Any process descriptions or blocks in flow charts should be understood as representing modules, segments, or portions of code which include one or more executable instructions for implementing specific logical functions or steps in the process. Alternate implementations are included, and it will be clear that functions may be executed out of order from that shown or discussed, including substantially concurrently or in reverse order, depending on the functionality involved. Accordingly, the apparatus components and method steps have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

Embodiments of the disclosure do not recite the implementation of any commonplace business method aimed at processing business information, nor do they apply a known business process to the particular technological environment of the Internet. Moreover, embodiments of the disclosure do not create or alter contractual relations using generic computer functions and conventional network operations. Quite to the contrary, embodiments of the disclosure employ methods that, when applied to electronic device and/or user interface technology, improve the functioning of the electronic device itself by and improving the overall user experience to overcome problems specifically arising in the realm of the technology associated with electronic device user interaction.

It will be appreciated that embodiments of the disclosure described herein may be comprised of one or more conventional processors and unique stored program instructions that control the one or more processors to implement, in conjunction with certain non-processor circuits, some, most, or all of the functions of querying, with a communication device, a companion device in communication across a wireless electrical communication channel with the electronic device to determine a companion device type, receiving an EDID extension comprising one of a field of view, pixel density, and/or interpupillary distance, determining, with one or more processors operable with the communication device, that the companion device consists of a wearable glass projection device when one or more of the field of view, the pixel density, and/or the interpupillary distance has a non-zero value, rendering content for the wearable glass projection device using the one or more of the field of view, the primary display, and/or the interpupillary distance, and transmitting the rendered content to the wearable glass projection device as described herein. The non-processor circuits may include, but are not limited to, a radio receiver, a radio transmitter, signal drivers, clock circuits, power source circuits, and user input devices.

As such, these functions may be interpreted as steps of a method to perform identifying a companion device electronically in communication with the wireless communication device as being a wearable glass projection device when a received EDID extension from the companion device includes a non-zero field of view, pixel density, and/or interpupillary distance value, rendering content for the wearable glass projection device as a function of the non-zero field of view, pixel density, and/or interpupillary distance value, and applying a rendering adjustment to the content as a function of optical data associated with a user of the electronic device stored in the non-transient memory device. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used. Thus, methods and means for these functions have been described herein. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ASICs with minimal experimentation.

Embodiments of the disclosure are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions.

As used herein, components may be "operatively coupled" when information can be sent between such components, even though there may be one or more intermediate or intervening components between, or along the connection path. The terms "substantially," "essentially," "approximately," "about," or any other version thereof, are defined as being close to as understood by one of ordinary skill in the art, and in one non-limiting embodiment the term is defined to be within ten percent, in another embodiment within five percent, in another embodiment within one percent and in another embodiment within one-half percent. The term "coupled" as used herein is defined as connected, although not necessarily directly and not necessarily mechanically. Also, reference designators shown herein in parenthesis indicate components shown in a figure other than the one in discussion. For example, talking about a device (10) while discussing figure A would refer to an element, 10, shown in figure other than figure A.

Embodiments of the disclosure provide an electronic device that is operable with one or more embodiments companion devices. Examples of such companion devices include monitors, projectors, and wearable glass projection devices. Examples of wearable glass projection devices include augmented reality companion devices and virtual reality companion devices.

In one or more embodiments, once the communication device of the electronic device establishes an electrical communication channel with a companion device, the communication device queries the companion device to determine whether the companion device is a projector, a monitor, or a wearable glass projection device. In one or more embodiments, the querying process comprises the exchange of EDID. In particular, in one or more embodiments one or more processors of the electronic device determine, in response to receiving EDID and an extension of the EDID in response to the query, whether the companion device is the projector, the monitor, or the wearable glass projection device by extracting a display size from the EDID and a field of view from the extension of the EDID.

Embodiments of the disclosure contemplate that the specifications differ between companion devices with which the electronic device may be operable. A monitor may have a non-zero display size but is generally not thought of as having a "field of view." Instead, monitor sizes are specified as having a length and width selected for users who are seated approximately four to eight feet from the monitor.

The same cannot be said for a wearable glass projection device such as an augmented reality companion device or virtual reality companion device. What the user sees is neither related to the physical size of the image generation component or a viewing area that is visible by the user. Instead, embodiments of the disclosure find it far more favorable to speak of specifications for a wearable glass projection device in terms of field of view or pixel density. Projectors, meanwhile, simply project with display size being a function of the distance between the projector and the projection surface.

Embodiments of the disclosure also contemplate that wearable glass projection devices can be coupled to a wide range of source devices, examples of which include computers, smartphones, tablet computers, set-top boxes, gaming devices, and multimedia players. When such a source device is connected to a wearable glass projection device, the source device provides images and sounds signals to the wearable glass projection device. The wearable glass projection device, in turn, then delivers images and sounds to an environment of the system defined by the source device, the wearable glass projection device, and the display data channel coupling the two together.

Indeed, many modern electronic devices are equipped with a content redirection feature. Using smartphones manufactured by Motorola Mobility.sup.™ as one illustrative example, some models are equipped with their Ready For-.sup.™, which is a feature that allows the Ready For.sup.™ device to act as a source device and connect to a wearable glass projection device such as a pair of augmented reality glasses or a virtual reality headset capable of presenting imagery to the eyes of a wearer. Using the Ready For.sup.™ feature, users can stream video content to the perceived "display" of the wearable glass projection device with no loss in performance. Illustrating by example, when rendered properly the resolution of the images presented by the wearable glass projection device is incredibly high in definition with a frame rate that presents content without flicker or distortion.

While the Ready For.sup.™ feature does not require a cable or a docking station, many electronic devices do require a physical connection in the form of a display data channel between the source device and the wearable glass projection device for a content redirection feature to work properly. To wit, many standards such as the highly popular and ubiquitous high-definition multimedia interface (HDMI) interface standard require a physical wire be connected between a source device and a display device for content redirection to work. Additionally, even some users of advanced content redirection technologies such as Ready For.sup.™ even prefer to use a docking station and/or physical cable to couple their electronic device to a content presentation companion device because a physical cable defining a display data channel invariably offers a more reliable and faster data connection than do most wireless connections. To be sure, coupling a smartphone having Ready For.sup.™ capability to a monitor having a defined display size is a quite popular way to view content on a larger display.

For content to be displayed properly, the source device must render the content in accordance with the capabilities of the companion device. With rectangular screens such as televisions and monitors, this is easy as each television or monitor has an inherent display size, with the display being a fixed distance from the light emitting elements that present content, images, and other information on the display. The display size is defined as EDID included in the base EDID structure, thereby allowing a source device to quickly and easily determine how to render content for a connected content presentation companion device.

Such a determination is not as straightforward with a wearable glass projection device. This is true because a wearable glass projection device does not have a physical screen with a defined display size. Instead, a wearable glass projection device such as an augmented reality companion device or a virtual reality companion device will include an image generation device, one example of which is a projector that projects light through one or more lenses for each eye of the wearer. In many cases, this image generation device and corresponding lenses are situated only a few inches from the eyes of a user when the user is wearing the wearable glass projection device. What the user sees is neither related to the physical size of the image generation component or a viewing area that is visible by the user.

Embodiments of the disclosure contemplate that for an optimal user experience, it is desirable to render content uniquely for the specific type of wearable glass projection device that will be presenting the rendered content. As different wearable glass projection devices have different constructions and specifications, there is not a "one size fits all" format for content rendering that can be used for all wearable glass projection devices. Slice assignments of the content should be assigned to the proper lens to avoid dyslexic projections. The field of view of the wearable glass projection device should be considered when the content is rendered. Additionally, since the lenses used with each eye can be situated within the wearable glass projection device so that they correspond to an interpupillary distance of the wearer, this factor too should be considered when rendering content.

Advantageously, embodiments of the disclosure offer two distinct functions for situations when a companion device is in communication with a communication device of an electronic device. First, one or more processors can determine what type of companion device is communicating with the electronic device, and whether that companion device in communication with the electronic device is a wearable glass projection device. In one or more embodiments, the one or more processors do the latter by receiving EDID and one or more extensions of the EDID in response to a query and extracting a display size having a zero value and one or more of a field of view, pixel density, and/or an interpupillary distance having a non-zero value from the one or more extensions from the EDID.

Second, the one or more processors can then render content for the wearable glass projection device using this information. Illustrating by example, in one or more embodiments the one or more processors obtain slice assignments for each lens of the wearable glass projection device from the EDID. The one or more processors can then render content in accordance with the slice assignments and the one or more of the field of view, the primary display, and/or the interpupillary distance and can thereafter cause the communication device to transmit the rendered content to the wearable glass projection device.

It should be noted that, as is well-understood by those of ordinary skill in the art, an "interpupillary distance" measures the distance between the centers of the eyes of a person. As related to embodiments of the disclosure, an "interpupillary distance" refers to the positions of the lenses within the wearable glass projection device, with lenses being spaced farther apart having a larger interpupillary distance, while lenses positioned closer together have a smaller interpupillary distance. In one or more embodiments, the interpupillary distance described herein is expressed as a distance between centers of the lenses. In other embodiments, the interpupillary distance is expressed as a default measurement combined with an adjustment measurement per lens.

Embodiments of the disclosure contemplate that that configuring a wearable glass projection device that has a lens interpupillary distance that matches the interpupillary distance of the wearer provides an optimal user experience in that the perception of images is clearer and eye strain is reduced. Embodiments of the disclosure also contemplate that assigning content slices to the proper eye is critical in making the content understandable. Embodiments of the disclosure further contemplate that content can optimally be presented by a wearable glass projection device when that content is rendered in accordance with a field of view or pixel density that matches the capabilities of the wearable glass projection device. Moreover, since the lenses focus images from the image generation device at their optical center, by adjusting the interpupillary distance between the lenses, this optical center can be tuned for a particular user so that the user can obtain their most comfortable view. This works to reduce blurred images, dizziness, and eye strain.

Accordingly, a first feature offered by embodiments of the disclosure is advantageously a two-specification "code" that allows an electronic device to quickly, efficiently, and automatically determine the type of companion device with which it is communicating. Illustrating by example, in one or more embodiments one or more processors of the electronic device determine that the companion device is a monitor anytime the display size received in EDID has a non-zero value. By contrast, the one or more processors determine that the companion device is a projector when the display size received in the EDID and the field of view or pixel density or interpupillary distance received in the extension of the EDID are both zero. When the display size is zero and the field of view or pixel density or interpupillary distance is a non-zero value, the one or more processors determine that the companion device is a wearable glass projection device.

When the companion device is a monitor, the one or more processors can render content in accordance with the display size and can cause the communication device to transmit the rendered content to the monitor. When the companion device is the projector, the one or more processors can render content in accordance with a default projector parameter and transmit the rendered content to the projector.

Similarly, if the companion device is a wearable glass projection device, the one or more processors can determine whether the wearable glass projection device is an augmented reality companion device or a virtual reality companion device. The one or more processors can render augmented reality content in accordance with a variety of factors that ensures optimum viewability of the content by a user. In one or more embodiments, the one or more processors render the content in accordance with slice assignments extracted from EDID and one or more of the field of view, the pixel density, and/or the interpupillary distance. Thereafter, the one or more processors can cause the communication device to transmit the rendered augmented reality content to the augmented reality companion device, one example of which are augmented reality glasses.

Advantageously, embodiments of the disclosure write both field of view or pixel density data and the interpupillary distance associated with the physical configuration of the lenses of the wearable glass projection device to EDID extensions. The EDID extensions are then transmitted with EDID that includes the slice assignments to a source device in response to a communication device of the wearable glass projection device detecting establishment of a display data channel with the source device.

The transmission of the slice assignments, the field of view or pixel density, and the interpupillary distance information to a source device is advantageous because in current systems, wearable glass projection devices are identified only by their Universal Serial Bus (USB) identifier. Unless a source device understands explicitly how the wearable glass projection device is configured, content cannot be rendered properly. Accordingly, embodiments of the disclosure include specific information, namely, a pixel density or field of view and/or the interpupillary distance of the lenses of a wearable glass projection device in addition to the slice assignments that are included in EDID to optimize the rendering of content. Embodiments of the disclosure therefore advantageously allow for backwards compatibility of electronic devices with new wearable glass projection devices.

In one or more embodiments, a wearable glass projection device which is connectable to a source device comprises a projector. Lenses focus images from the projector at an image focus optical scenter that is a function of the interpupillary distance defined by the positions of the lenses in the wearable glass projection device.

The wearable glass projection device also includes one or more processors operable with the projector and a communication device operable with the one or more processors. In one or more embodiments, the one or more processors, in response to the communication device detecting establishment of a display data channel with the source device, create and EDID extension comprising an indication of the interpupillary distance and another EDID extension comprising pixel density or field of view and cause the communication device to transmit the EDID extensions to the source device using the display data channel.

Embodiments of the disclosure contemplate that these additional measurements, field of view, pixel density, and interpupillary distance, can be represented in a variety of ways. Illustrating by example, field of view is typically measured in degrees. Additionally, embodiments of the disclosure contemplate that pixel density can be used as an alternate specification for wearable glass projection device. In one or more embodiments, the pixel density is expressed in pixels per degree. In one or more embodiments the interpupillary distance is simply a measurement of distance, which can be expressed in inches, millimeters, and so forth. In other embodiments, each wearable glass projection device has a default interpupillary distance. Where this is the case, the interpupillary distance can be represented either as the default interpupillary distance plus an adjustment measurement representing a "plus" or "minus" distance adjustment for each lens.

Accordingly, embodiments of the disclosure can be used to identify the type of companion device when that companion device is operating as a content presentation companion device. Embodiments of the disclosure therefore provide a solution enabler that surfaces an interpupillary distance metric and a field of view or pixel density metric (in addition to slice assignments) for a wearable glass projection device to a source device by delivering EDID and one or more EDID extensions to the source device using the display data channel that is established between the source device and the wearable glass projection device. The source device can then easily access this information and properly render content for the wearable glass projection device.

Using logic programmed into the source device, the source device can even distinguish a wearable glass projection device from a projector or monitor since neither a projector nor monitor has either an interpupillary distance or a field of view/pixel density metric associated therewith. Embodiments of the disclosure therefore enhance the EDID standard by including one or more EDID extensions that include an indication of field of view or pixel density and another indication of an interpupillary distance of a wearable glass projection device that is in communication with a source device.

Using an augmented reality device as an example, in one or more embodiments an augmented reality device includes an augmented reality presentation device, a communication device, and one or more processors operable with the communication device and the augmented reality presentation device. In one or more embodiments the one or more processors, in response to the communication device establishing a display data channel, cause the communication device to transmit EDID and one or more EDID extensions.

In one or more embodiments, the EDID include slice assignments, while the EDID extension(s) comprise augmented reality content rendering parameters of the augmented reality presentation device using the display data channel.

In one or more embodiments, the Augmented reality content rendering parameter can be expressed as a field of view or pixel density and an interpupillary distance associated with a physical configuration of the augmented reality device defined by positions of the lenses of the augmented reality device. In one or more embodiments, the one or more processors cause the communication device to transmit an EDID file comprising an EDID extension flag indicating that the one or more EDID extensions are included.

In one or more embodiments, an electronic device determines that the electronic device is connected to a companion device. This determination can be done by querying EDID of the companion device in one or more embodiments. In one or more embodiments, the EDID comprises a monitor size and slice assignments while extensions of the EDID comprises fields indicating a field of view or pixel density and other fields indicating interpupillary distance.

Embodiments of the disclosure contemplate that geometrically speaking, a wearable glass projection device such as an augmented reality companion device or a virtual reality companion device will include an image generation device that is just a few inches from the eyes of a user in many cases. However, that same device will have a field of view allowing a display size similar to a large monitor situated several feet away. Advantageously, by rendering content for the wearable glass projection device in accordance with field of view or pixel density extracted from an extension of EDID, in combination with interpupillary distance data as described above, an electronic device can tune the rendering to achieve the optimal user interface to be rendered by the wearable glass projection device.

This occurs because, for wearable glass projection devices, first operating condition is a function of distance, and the physical size of the actual projection is calculated using the size of the image generation device and an optimal distance at which the content should be viewed. Additionally, the interpupillary distance ensures that the rendered content is suitable for the spacing between lenses when considered in relation to the slice assignments. Accordingly, using the field of view or pixel density parameter, combined with the interpupillary distance and slice assignments, virtual reality or augmented reality content simply looks perfect every time.

Embodiments of the disclosure contemplate that for a wearable glass projection device, field of view is a principal design key performance indicator (KPI). Accordingly, for a given wearable glass projection device design, the field of view is known and can be stored in an extension of EDID. This is advantageous because directly calculating a field of view for a particular wearable glass projection device is generally not straightforward due to various possible design elements that may be present in the wearable glass projection device, as well as the physical distance from the eye to the image rendering surface. Additionally, there may be mirrors, lenses, and so forth along the optical path that complicate the calculation.

For this reason, embodiments of the disclosure advantageously include the field of view (or an equivalent pixel density) in an extension of the EDID. Identification logic can then be employed that determines a companion device is a monitor when the display size is non-zero. If the display size is zero and the field of view is zero and the interpupillary distance is zero, the companion device is a projector. If the display size is zero and the field of view is non-zero and the interpupillary distance is non-zero, the companion device is a wearable glass projection device, and so forth. Embodiments of the disclosure advantageously allow for backwards compatibility of electronic devices with new wearable glass projection devices.

In one or more embodiments, an electronic device comprises a communication device, a non-transient memory, and one or more processors operable with the communication device and the non-transient memory. In one or more embodiments, the one or more processors cause, in response to the communication device detecting establishment of an electrical communication channel with a companion device, the communication device to query the companion device to determine a companion device type.

In one or more embodiments, the one or more processors determine, in response to the communication device receiving EDID and one or more extensions of the EDID in response to the query, that eth companion device is a wearable glass projection device by extracting a display size having a zero value from the EDID and one or more of a field of view, pixel density, and/or interpupillary distance having a non-zero value from the one or more extensions of the EDID.

In one or more embodiments, the one or more processors can then obtain slice assignments from the EDID for the wearable glass projection device. The one or more processors can render content in accordance with the slice assignments and the one or more of the field of view, the pixel density, and/or the interpupillary distance. The one or more processors can then cause the communication device to transmit rendered content to the wearable glass projection device.

If, for example, the wearable glass projection device comprises augmented reality glasses, the one or more processors can render augmented reality content with a number of pixels per degree defined by the non-zero field of view and in accordance with both the slice assignments and interpupillary distance to create rendered augmented reality content. The one or more processors can then cause the wireless communication device to transmit the rendered augmented reality content to the augmented reality glasses. Other advantages offered by embodiments of the disclosure will be described below. Still others will be obvious to those of ordinary skill in the art having the benefit of this disclosure.

Turning now to FIG. 1, illustrated therein is one explanatory companion device 100 configured in accordance with one or more embodiments of the disclosure. The companion device 100 of FIG. 1 is a wearable glass projection device and in particular is an augmented reality companion device configured to operate in conjunction with an electronic device to provide augmented reality content to a user.

While the companion device 100 of FIG. 1 is shown as being an augmented reality companion device for explanatory purposes, wearable glass projection devices configured in accordance with embodiments of the disclosure can take other forms as well. Illustrating by example, as will be discussed in more detail below with reference to FIG. 4, in other embodiments a wearable glass projection device can be configured as a virtual reality companion device. Additionally, companion devices configured in accordance with embodiments of the disclosure do not have to be wearable glass projection devices. They can also be monitors, projectors, or other types of devices.

The augmented reality companion device of FIG. 1 is shown illustratively as being augmented reality glasses.

However, it should be noted that the augmented reality companion device could be configured in any number of other ways as well. Illustrating by example, augmented reality companion device could also be configured as any of sunglasses, goggles, masks, shields, or visors. Other forms of the augmented reality companion device will be obvious to those of ordinary skill in the art having the benefit of this disclosure.

The companion device 100 of FIG. 1 includes a frame 101 and one or more stems 102,103. Here, the one or more stems 102,103 comprise a first stem 102 and a second stem 103.

One or more lenses 104,105 can be disposed within the frame 101. The lenses 104,105 can be prescription or non-prescription, and can be clear, tinted, or dark.

In one or more embodiments the stems 102,103 are pivotable from a first position where they are situated adjacent to, and parallel with, the frame 101, to a second, radially displaced open position shown in FIG. 1. However, in other embodiments the stems 102,103 may be fixed relative to the frame 101. In still other embodiments, such as might be the case if the companion device 100 were configured as goggles, the stems 102,103 may be flexible or soft. For example, the stems of goggles are frequently elasticized fabric, which is soft, flexible, pliable, and stretchy. Other types of stems 102,103 will be obvious to those of ordinary skill in the art having the benefit of this disclosure.

In one or more embodiments the stems 102,103 attach to the frame 101 at a first end 108,109 and extend distally from the frame 101 to a second, distal end 110,126. In one embodiment, each stem 102,103 includes a temple portion 106 and an ear engagement portion 107. The temple portion 106 is the portion of the stem 102,103 passing from the frame 101 past the temple of a wearer, while the ear engagement portion 107 engages the wearer's ear to retain the augmented reality glasses to the wearer's head.

Since the companion device 100 is configured as an electronic device, one or both of the frame 101 and the stems 102,103 can comprise one or more electrical components. These electrical components are shown illustratively in a schematic block diagram 125 in FIG. 1. It will be clear to those of ordinary skill in the art having the benefit of this disclosure that the electrical components and associated modules can be used in different combinations, with some components and modules included and others omitted. Components or modules can be included or excluded based upon need or application.

The electronic components can include one or more processors 111. The one or more processors 111 can be disposed in one (or both) of the stems 102, 103 and/or the frame 101. The one or more processors 111 can be operable with a memory 112. The one or more processors 111, which may be any of one or more microprocessors, programmable logic, application specific integrated circuit device, or other similar device, are capable of executing program instructions and methods described herein. The program instructions and methods may be stored either on-board in the one or more processors 111, or in the memory 112, or in other computer readable media coupled to the one or more processors 111.

The one or more processors 111 can be configured to operate the various functions of the companion device 100, and also to execute software or firmware applications and modules that can be stored in a computer readable medium, such as memory 112. The one or more processors 111 execute this software or firmware, in part, to provide device functionality. The memory 112 may include either or both static and dynamic memory components, may be used for storing both embedded code and user data.

In one or more embodiments, the companion device 100 also includes an optional wireless communication device 113. Where included, the wireless communication device 113 is operable with the one or more processors 111 and is used to facilitate electronic communication with one or more electronic devices or servers or other communication devices across a network. Note that it is possible to combine the one or more processors 111, the memory 112, and the wireless communication device 113 into a single device, or alternatively into devices having fewer parts while retaining the functionality of the constituent parts.

The wireless communication device 113, which may be one of a receiver or transmitter and may alternatively be a transceiver, operates in conjunction with the one or more processors 111 to electronically communicate through a communication network. For example, in one embodiment, the wireless communication device 113 can be configured to communicate through a traditional cellular network. Other examples of networks with which the communication circuit may communicate include proprietary networks and direct communication networks. In other embodiments, the wireless communication device 113 can communicate with near field or local area networks, infrared communication circuits, magnetic field modulation circuits, and Wi-Fi circuits. In one or more embodiments, the wireless communication device 113 can be configured to provide messaging functionality to deliver electronic messages to remote devices.

A battery 114 or other energy storage device can be included to provide power for the various components of the companion device 100. While a battery 114 is shown in FIG. 1, it will be obvious to those of ordinary skill in the art having the benefit of this disclosure that other energy storage devices can be used instead of the battery 114, including a micro fuel cell or an electrochemical capacitor. The battery 114 can include a lithium-ion cell, lithium polymer cell, or a nickel metal hydride cell, such cells having sufficient energy capacity, wide operating temperature range, large number of charging cycles, and long useful life. The battery 114 may also include overvoltage and overcurrent protection and charging circuitry. In one embodiment, the battery 114 comprises a small, lithium polymer cell.

In one or more embodiments, a photovoltaic device 115, such as a solar cell, can be included to recharge the battery 114. In one embodiment, the photovoltaic device 115 can be disposed along the temple portion 106 of the stems 102,103. In this illustrative embodiment, two solar cells are disposed in the temple portion 106 of each stem 102,103, respectively.

Other components 116 can be optionally included in the companion device 100 as well. For example, in one embodiment one or more microphones can be included as audio capture devices 117. These audio capture devices can be operable with the one or more processors 111 to receive voice input. Additionally, in one or more embodiments the audio capture devices 117 can capture ambient audio noise. Signals corresponding to captured audio can be transmitted to an electronic device in communication with the companion device 100 or a server or cloud-computing device. The other component 116 can additionally include loudspeakers for delivering audio content to a user wearing the companion device 100.

The other components 116 can also include a motion generation device for providing haptic notifications or vibration notifications to a user. For example, a piezoelectric transducer, rotational motor, or other electromechanical device can be configured to impart a force or vibration upon the temple portion 106 of the stems 102,103, or alternatively along the frame 101. The motion generation device can provide a thump, bump, vibration, or other physical sensation to the user. The one or more processors 111 can be configured to actuate the motion generation device to deliver a tactile or vibration output alone or in combination with other outputs such as audible outputs.

Similarly, in one or more embodiments the companion device 100 can include a video capture device such as an imager. The imager can be disposed within the frame 101 or stems 102,103. In one or more embodiments, the video capture device can function as a to detect changes in optical intensity, color, light, or shadow in the near vicinity of the companion device 100. As with the audio capture device 117, captured video information can be transmitted to an electronic device, a remote server, or cloud-computing device.

Other sensors 119 can be optionally included in the companion device 100. One example of such a sensor is a global positioning system device for determining where the companion device 100 is located. The global positioning system device can communicate with a constellation of earth orbiting satellites or a network of terrestrial base stations to determine an approximate location. While a global positioning system device is one example of a location determination module, it will be clear to those of ordinary skill in the art having the benefit of this disclosure that other location determination devices, such as electronic compasses or gyroscopes, could be used as well.

The other sensors 119 can also include an optional user interface. The user interface can be used, for example, to activate the circuit components or turn them OFF, control sensitivity of the other sensors 119, and so forth. The user interface, where included, can be operable with the one or more processors 111 to deliver information to, and receive information from, a user. The user interface can include a rocker switch, slider pad, button, touch-sensitive surface, or other controls, and optionally a voice command interface. These various components can be integrated together.

In one or more embodiments, an audio output device 120, such as a loudspeaker or other transducer, can deliver audio output to a user. For example, piezoelectric transducers can be operably disposed within the stems 102,103. Actuation of the piezoelectric transducers can cause the stems 102,103 to vibrate, thereby emitting acoustic output. More traditional audio output devices 120, such as loudspeakers, can be used as well.

The other components 116 can optionally include a haptic device providing haptic feedback to a user. The haptic device can include a motion generation device to deliver a tactile response to the user. For example, a piezoelectric transducer or other electromechanical device can be included in the stems 102,103. The transducer can actuate to impart a force upon the user's head to provide a thump, bump, vibration, or other physical sensation to the user. The inclusion of both the audio output device 120 and the haptic device allows both audible and tactile feedback to be delivered.

In one or more embodiments, the companion device 100 includes an augmented reality image presentation device 121 operable to deliver augmented reality imagery to a user. The augmented reality image presentation device 121 can be operable with a projector 122. In the illustrative embodiment of FIG. 1, the frame 101 supports the projector 122. In one or more embodiments the projector 122 is configured to deliver images to a holographic optical element when the companion device 100 is operating in an augmented reality mode of operation.

In one embodiment, the projector 122 is a modulated light projector operable to project modulated light images along a surface or holographic optical element. In another embodiment, the projector 122 is a thin micro projector. In another embodiment, the projector 122 can comprise a laser projector display module. Other types of projectors will be obvious to those of ordinary skill in the art having the benefit of this disclosure.

In one or more embodiments, the projector 122 can include a lens and a spatial light modulator configured to manipulate light to produce images. The projector 122 can include a light source, such as a single white light emitting diode, multiple separate color light emitting diodes, or multiple separate color laser diodes that deliver visible light to the spatial light modulator through a color combiner. The augmented reality image presentation device 121 can drive the spatial light modulator to modulate the light to produce images. The spatial light modulator can be optically coupled (e.g., by free space propagation) to the lens and/or a beam steerer. Where used, a beam steerer serves to steer a spatially modulated light beam emanating from the spatial light modulator through the lens to create images.

Embodiments of the disclosure contemplate that the specifications differ between companion devices with which an electronic device may be operable. A monitor may have a non-zero display size but is generally not thought of as having a "field of view." The same cannot be said for a wearable glass projection device such as the companion device 100 shown in FIG. 1 or the companion device (400) shown below in FIG. 4. What the user sees when the augmented reality image presentation device 121 is operational is neither related to the physical size of the augmented reality image presentation device 121 or a viewing area that is visible by the user. Instead, embodiments of the disclosure find it far more favorable to speak of specifications for the augmented reality image presentation device 121 in terms of field of view or pixel density.

What's more, augmented reality companion devices and virtual reality companion devices are defined by lenses 104, 105 placed in front of the eyes of a user. Accordingly, the companion device 100 of FIG. 1 also has an interpupillary distance associated with a physical configuration of the wearable glass projection device. As noted above, in one or more embodiments the companion device 100 comprises a projector 122. The lenses 104,105 focus images from the projector 122 at an image focus optical center that is a function of an interpupillary distance defined by positions of the lenses 104,105 within the wearable glass projection device. Accordingly, for proper content presentation, the content should be rendered in accordance with the interpupillary distance defined by the physical construct of the companion device 100 and/or its lenses 104,105.

Embodiments of the disclosure contemplate that for wearable glass projection device such as the companion device 100 of FIG. 1, field of view and interpupillary distance define principal KPIs. Accordingly, for a given augmented reality image presentation device 121 design, the field of view and interpupillary distance are known and can be stored in one or more extensions 128,129 of EDID 127 that is stored in the memory 112 and delivered to another electronic device via the communication device 113, either automatically or in response to queries from the other electronic device. This is advantageous because when the other electronic device is delivering rendered content for presentation by the augmented reality image presentation device 121, this content can be rendered in accordance with a specified field of view and interpupillary distance for proper presentation.

For this reason, embodiments of the disclosure advantageously include the field of view (or an equivalent pixel density) metric in an extension 128 of the EDID 127 stored in the memory 112 of the companion device 100. Additionally, embodiments of the disclosure include the interpupillary distance metric in another extension 129 of the EDID 127 stored in the memory 112 of the companion device 100. Identification logic can then be employed that determines the companion device is a wearable glass projection device due to the fact that the display size is zero and the field of view and/or interpupillary distance are non-zero.

Advantageously, embodiments of the disclosure write both the interpupillary distance associated with the physical configuration of the lenses 104,105 of the companion device 100 and the field of view (or equivalent pixel density) associated with the projector 122 to EDID extensions 128, 129. The EDID extensions 128,129 can then be transmitted to a source device in response to a communication device 113 of the companion device 100 detecting establishment of a display data channel with the source device.

In one or more embodiments, the indication of the interpupillary distance is expressed as a distance measurement. For instance, the interpupillary distance can be measured in millimeters. In other embodiments, the interpupillary distance is expressed as a default measurement associated with a wearable glass projection device combined with an adjustment measurement provided on a per-lens basis. If the default measurement were five centimeters, for example, an adjustment measurement for the right lens might be plus two millimeters while an adjustment measurement for the left lens might be minus three millimeters, and so forth.

In addition to providing interpupillary distance and field of view or pixel density in EDID extensions 128,129, embodiments of the disclosure also populate other fields of an EDID 127 with information associated with the companion device 100. Illustrating by example, in one or more embodiments the slice assignments associated with each lens 104,105 of the companion device 100 are written to the EDID 127 as well.

Accordingly, embodiments of the disclosure advantageously provide a three-metric "code" that allows a source device to quickly, efficiently, and automatically determine the physical configuration of the companion device 100 with which it is communicating. Embodiments of the disclosure advantageously allow for backwards compatibility of electronic devices with new wearable glass projection devices.

In one or more embodiments, the one or more processors 111, in response to the communication device receiving an EDID request, cause the communication device 113 to transmit an EDID file 127 to a source device. In one or more embodiments, slice assignments for each lens 104,105 of the companion device 100 are written to the EDID file 127. However, the one or more processors 111 also cause the communication device to transmit the EDID extensions 128,129 with the EDID 127 in response to the EDID request. As noted, the EDID extensions include the indications of the field of view (or equivalent pixel density) and interpupillary distance. As noted above, the interpupillary distance can be represented as a singular distance or a default distance with adjustment measurements for the interpupillary distance or each lens on a per lens basis.

In the illustrative embodiment of FIG. 1, the frame 101 supports the projector 122. In one or more embodiments the projector 122 is configured to deliver images to a holographic optical element when the companion device 100 is operating in an augmented reality mode of operation.

In one or more embodiments, for a given augmented reality image presentation device 121 design, the interpupillary distance can be detected by the one or more sensors 119 of the companion device 100 when the adjustment device 130 is manipulated. This interpupillary distance can then be stored in an EDID extension 129 that is stored in the memory 112 and that can be delivered with an EDID 127 to a source device, along with the field of view or pixel density written to the other EDID extension 128, and along with the slice assignments written to the EDID 127. This delivery can occur via the communication device 113, either automatically or in response to queries from the source device. This is advantageous because when the source device is delivering rendered content for presentation by the augmented reality image presentation device 121, this content can be rendered in accordance with a specified interpupillary distance, field of view, and slice assignments for proper presentation.

For this reason, embodiments of the disclosure advantageously include the field of view or pixel density, slice assignments, and interpupillary distance metric in EDID data. Not only do these metrics allow the source device to properly format content for presentation by the augmented reality image presentation device 121, but it can also allow identification logic in the source device to determine that the companion device 100 of FIG. 1 is indeed a wearable glass projection device. In one or more embodiments, this determination is made any time the interpupillary distance or field of view or pixel density is set in the EDID extensions 128,129.

In one or more embodiments, the companion device 100 includes a companion device display integration manager 124. The companion device display integration manager 124 can be used to communicate with a companion electronic device.

Illustrating by example, in one or more embodiments the companion device 100 comes in different sizes. When another electronic device wishes to determine whether the size of the companion device 100 is below a predefined size threshold, the other electronic device may interrogate the companion device 100 using the communication device 113.

The companion device display integration manager 124 may provide size, user profile, or other information associated with the companion device 100 to the other electronic device using the communication device 113 in response. This is addition to the ability to deliver EDID 127 and/or extensions 128,129 of the EDID 127 including a non-zero value for the field of view (or alternatively pixel density) and interpupillary distance.

Additionally, when another device transmits event notifications, subtitles, or other contextual information to the companion device 100, the companion device display integration manager 124 can deliver that information to the augmented reality image presentation device 121 for presentation to the user as an augmented reality experience via the projector 122.

Figure 2:
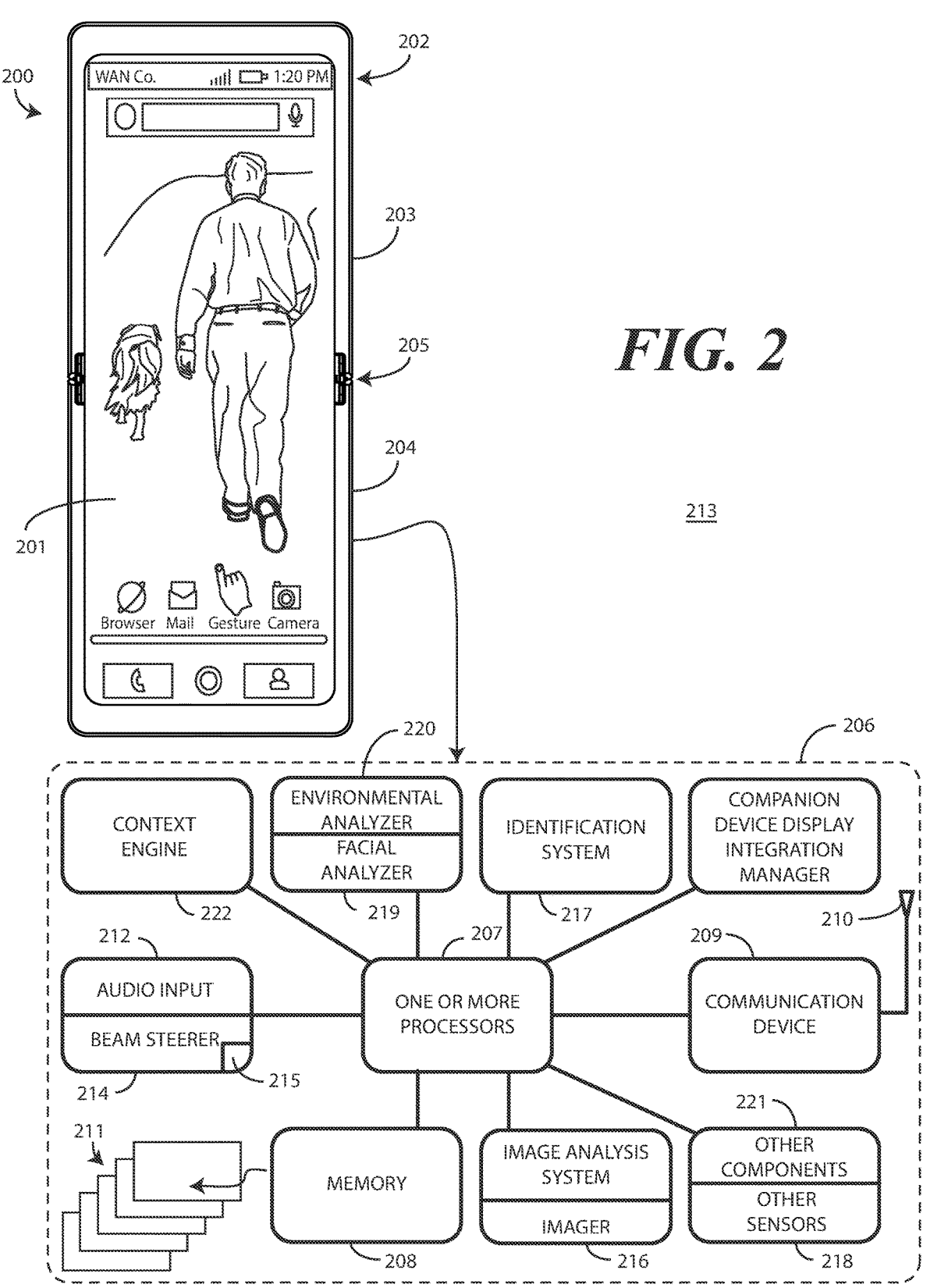
FIG. 2 illustrates one explanatory electronic device in accordance with one or more embodiments of the disclosure.

The companion device 100 of FIG. 1 can operate as a stand-alone electronic device in one or more embodiments. However, in other embodiments, the companion device 100 can operate in tandem with an electronic device, via wireless electronic communication using the wireless communication device 113 or via a wired connection channel 123 to form an augmented reality system. Turning now to FIG. 2, illustrated therein is one such electronic device 200.

The electronic device 200 of FIG. 2 is a portable electronic device and is shown as a smartphone for illustrative purposes. However, it should be obvious to those of ordinary skill in the art having the benefit of this disclosure that other electronic devices may be substituted for the explanatory smart phone of FIG. 2. For example, the electronic device 200 could equally be a conventional desktop computer, palm-top computer, a tablet computer, a gaming device, a media player, or other device.

This illustrative electronic device 200 includes a display 201, which may optionally be touch-sensitive. Users can deliver user input to the display 201, which serves as a user interface for the electronic device 200. In one embodiment, users can deliver user input to the display 201 of such an embodiment by delivering touch input from a finger, stylus, or other objects disposed proximately with the display 201. In one embodiment, the display 201 is configured as an active-matrix organic light emitting diode (AMOLED) display. However, it should be noted that other types of displays, including liquid crystal displays, would be obvious to those of ordinary skill in the art having the benefit of this disclosure.

The explanatory electronic device 200 of FIG. 2 also includes a device housing 202. In one embodiment, the device housing 202 includes two housing members, namely, a first device housing 203 that is coupled to a second device housing 204 by a hinge 205 such that the first device housing 203 is pivotable about the hinge 205 relative to the second device housing 204 between a closed position and an axially displaced open position. In other embodiments, the device housing 202 will be rigid and will include no hinge.

In still other embodiments, the device housing 202 will be manufactured from a flexible material such that it can be bent and deformed. Where the device housing 202 is manufactured from a flexible material or where the device housing 202 includes a hinge, the display 201 can be manufactured on a flexible substrate such that it bends. In one or more embodiments, the display 201 is configured as a flexible display that is coupled to the first device housing 203 and the second device housing 204, spanning the hinge 205. Features can be incorporated into the device housing 202, including control devices, connectors, and so forth.

Also shown in FIG. 2 is an explanatory block diagram schematic 206 of the explanatory electronic device 200. In one or more embodiments, the block diagram schematic 206 is configured as a printed circuit board assembly disposed within the device housing 202 of the electronic device 200. Various components can be electrically coupled together by conductors, or a bus disposed along one or more printed circuit boards.

The illustrative block diagram schematic 206 of FIG. 2 includes many different components. Embodiments of the disclosure contemplate that the number and arrangement of such components can change depending on the particular application. Accordingly, electronic devices configured in accordance with embodiments of the disclosure can include some components that are not shown in FIG. 2, and other components that are shown may not be needed and can therefore be omitted.

In one embodiment, the electronic device includes one or more processors 207. In one embodiment, the one or more processors 207 can include an application processor and, optionally, one or more auxiliary processors. One or both of the application processor or the auxiliary processor(s) can include one or more processors. One or both of the application processor or the auxiliary processor(s) can be a microprocessor, a group of processing components, one or more ASICs, programmable logic, or other type of processing device.

The application processor and the auxiliary processor(s) can be operable with the various components of the block diagram schematic 206. Each of the application processor and the auxiliary processor(s) can be configured to process and execute executable software code to perform the various functions of the electronic device with which the block diagram schematic 206 operates. A storage device, such as memory 208, can optionally store the executable software code used by the one or more processors 207 during operation.

In this illustrative embodiment, the block diagram schematic 206 also includes a communication device 209 that can be configured for wired or wireless communication with one or more other devices or networks. The networks can include a wide area network, a local area network, and/or personal area network. The communication device 209 may also utilize wireless technology for communication, such as, but are not limited to, peer-to-peer or ad hoc communications such as HomeRF, Bluetooth and IEEE 802.11, and other forms of wireless communication such as infrared technology. The communication device 209 can include wireless communication circuitry, one of a receiver, a transmitter, or transceiver, and one or more antennas 210.

In one embodiment, the one or more processors 207 can be responsible for performing the primary functions of the electronic device with which the block diagram schematic 206 is operational. For example, in one embodiment the one or more processors 207 comprise one or more circuits operable with the display 201 to present presentation information to a user. The executable software code used by the one or more processors 207 can be configured as one or more modules 211 that are operable with the one or more processors 207. Such modules 211 can store instructions, control algorithms, and so forth.

In one or more embodiments, the block diagram schematic 206 includes an audio input/processor 212. The audio input/processor 212 is operable to receive audio input from an environment 213 about the electronic device 200. The audio input/processor 212 can include hardware, executable code, and speech monitor executable code in one embodiment. The audio input/processor 212 can be operable with one or more predefined identification references stored in memory 208. With reference to audio input, the predefined identification references can comprise representations of basic speech models, representations of trained speech models, or other representations of predefined audio sequences that are used by the audio input/processor 212 to receive and identify voice commands that are received with audio input captured by an audio capture device. In one embodiment, the audio input/processor 212 can include a voice recognition engine. Regardless of the specific implementation utilized in the various embodiments, the audio input/processor 212 can access various speech models stored with the predefined identification references to identify speech commands, languages being spoken, and other information.

The audio input/processor 212 can include a beam steering engine 214 comprising one or more microphones 215. Input from the one or more microphones 215 can be processed in the beam steering engine 214 such that the one or more microphones define a virtual microphone. This virtual microphone can define an acoustic reception cone that can be virtually "steered" around the electronic device 200. Alternatively, actual steering can occur as well, such as switching between a left and right microphone or a front and back microphone or switching various microphones ON and OFF individually. In one or more embodiments, two or more microphones 215 can be included for selective beam steering by the beam steering engine 214.

Illustrating by example, a first microphone can be located on a first side of the electronic device 200 for receiving audio input from a first direction, while a second microphone can be placed on a second side of the electronic device 200 for receiving audio input from a second direction. These microphones can be "steered" by selectively turning them ON and OFF.

The beam steering engine 214 can then select between the first microphone and the second microphone to beam steer audio reception toward an object, such as a user delivering audio input. This beam steering can be responsive to input from other sensors, such as imagers, facial depth scanners 219, thermal sensors, or other sensors. For example, an imager 216 can estimate a location of a person's face and deliver signals to the beam steering engine 214 alerting it in which direction to focus the acoustic reception cone and/or steer the first microphone and the second microphone, thereby adding confirmation to audio steering and saving time. Where multiple people are around the electronic device 200, this steering advantageously directs a beam reception cone toward a particular person so that languages spoken, language preferences, and other information about the person's speech can be ascertained.

Alternatively, the beam steering engine 214 processes and combines the signals from two or more microphones to perform beam steering. The one or more microphones 215 can be used for voice commands and/or for language recognition. In response to control of the one or more microphones 215 by the beam steering engine 214, a user location direction can be determined. The beam steering engine 214 can then select between the first microphone and the second microphone to beam steer audio reception toward the user. Alternatively, the audio input/processor 212 can employ a weighted combination of the microphones to beam steer audio reception toward the user.

The one or more processors 207 can perform filtering operations on audio input received by the audio input/processor 212. For example, in one embodiment the one or more processors 207 can filter the audio input into identifiable audio input, i.e., first audio input, and other audio input that is not identifiable, i.e., second audio input.

Various sensors 218 can be operable with the one or more processors 207. One example of a sensor that can be included with the various sensors 218 is a touch sensor. The touch sensor can include a capacitive touch sensor, an infrared touch sensor, resistive touch sensors, or another touch-sensitive technology. Capacitive touch-sensitive devices include a plurality of capacitive sensors, e.g., electrodes, which are disposed along a substrate. Each capacitive sensor is configured, in conjunction with associated control circuitry, e.g., the one or more processors 207, to detect an object in close proximity with—or touching—the surface of the display 201 or the device housing 202 of the electronic device 200 by establishing electric field lines between pairs of capacitive sensors and then detecting perturbations of those field lines.

Another example of a sensor that can be included with the various sensors 218 is a geo-locator that serves as a location detector. In one embodiment, location detector is able to determine location data when authenticating a user. Location can be determined by capturing the location data from a constellation of one or more earth orbiting satellites, or from a network of terrestrial base stations to determine an approximate location. The location detector may also be able to determine location by locating or triangulating terrestrial base stations of a traditional cellular network, or from other local area networks, such as Wi-Fi networks.

Another example of a sensor that can be included with the various sensors 218 is an orientation detector operable to determine an orientation and/or movement of the electronic device 200 in three-dimensional space. Illustrating by example, the orientation detector can include an accelerometer, gyroscopes, or other device to detect device orientation and/or motion of the electronic device 200. Using an accelerometer as an example, an accelerometer can be included to detect motion of the electronic device. Additionally, the accelerometer can be used to sense some of the gestures of the user, such as one talking with their hands, running, or walking.

The orientation detector can determine the spatial orientation of an electronic device 200 in three-dimensional space by, for example, detecting a gravitational direction. In addition to, or instead of, an accelerometer, an electronic compass can be included to detect the spatial orientation of the electronic device relative to the earth's magnetic field. Similarly, one or more gyroscopes can be included to detect rotational orientation of the electronic device 200.

An identification system 217 is operable with the one or more processors 207. In one or more embodiments, the identification system 217 is operable with both the one or more processors 207 and the communication device 209. The identification system 217, operating with the one or more processors 207, can cause the communication device 209, in response to the communication device 209 detecting establishment of an electrical communication channel with a companion device (100) such as that described above with reference to FIG. 1, to query the companion device (100) to determine what type of device the companion device (100) is. Illustrating by example, the identification system 217 can cause the communication device 209 to query the companion device (100) to determine whether the companion device (100) is a projector, a monitor, or a wearable glass projection device.

In one or more embodiments, this querying results in the companion device (100) retrieving EDID (127) and/or extensions (128,129) of EDID (127) from a memory (112) and transmitting it to the electronic device 200 in response to the query. In one or more embodiments, the identification system 217 and one or more processors 207 then determine, in response to the communication device 209 receiving the EDID (127) and extensions (128,129) of the EDID (127) whether the companion device (100) is a projector, a monitor, or the wearable glass projection device of FIG. 1 by extracting a display size from the EDID (127) a field of view (or equivalent pixel density) from an extension (128) of the EDID (127), and an interpupillary distance from another extension (129) of the EDID (127).

In one or more embodiments, the identification system 217 and one or more processors 207 determine that the companion device is a monitor when the display size is a non-zero value. When this occurs, the one or more processors 207 can render content in accordance with the display size and can cause the communication device 209 to transmit the rendered content to the monitor.

In one or more embodiments, the identification system 217 and one or more processors 207 determine that the companion device is a projector when the display size and the field of view are both zero. When this occurs, the one or more processors 207 can render content in accordance with a default projector parameter stored in the memory 208. The one or more processors 207 can then cause the communication device 209 to transmit the rendered content to the projector.

In one or more embodiments, the identification system 217 and one or more processors 207 determine the companion device (100) is a wearable glass projection device when the display size is zero and the field of view and interpupillary distance are each non-zero values. In one or more embodiments, when this occurs the one or more processors 207 obtain slice assignments for each lens (104,105) of the companion device (100) form the EDID (127).

Thereafter, the one or more processors 207 can render content in accordance with the slice assignments, the field of view value, and the interpupillary distance. The one or more processors 207 can then cause the communication device 209 to transmit the rendered content to the wearable glass projection device.

The identification system 217 and one or more processors 207 can also determine, in response to the communication device 209 receiving the extensions (128,129) of the EDID (127) in response to the query, that the companion device (100) is the wearable glass projection device by extracting the field of view having the non-zero value from an extension (128) of the EDID (127) and an interpupillary distance having a non-zero value from another extension (129) of the EDID (127). An example of EDID will be illustrated below with reference to FIG. 8. An example of an extension (128) of the EDID (127) will be described below with reference to FIG. 9. An example of another extension (129) of the EDID (127) will be described below with reference to FIG. 10.

In one or more embodiments, when the companion device (100) comprises augmented reality glasses, as would be the case if the companion device (100) were that of FIG. 1 above, the one or more processors 207 can render augmented reality content in accordance with the slice assignments extracted from the EDID (127), the field of view extracted from the extension (128) of the EDID (127), and the interpupillary distance extracted from the other extension (128) of the EDID (127). The one or more processors 207 can then cause the communication device 209 to transmit the rendered augmented reality content to the augmented reality glasses.

While field of view is a fantastic parameter to include in the extension (128) of the EDID (127), embodiments of the disclosure are not so limited. In other embodiments, a pixel density can be used in place of, or in combination with, the field of view. Accordingly, in one or more embodiments the identification system 217 and one or more processors 207 determine, in response to the communication device 209 receiving the extension (128) of the EDID (127) in response to the query, that the companion device is a wearable glass projection device by extracting a pixel density having a non-zero value from the extension (128) of the EDID (127) and an interpupillary distance having a non-zero value from another extension (129) of the EDID (127). In one or more embodiments, the pixel density is expressed in pixels per degree.

In one or more embodiments, the identification system 217 is operable with the one or more processors 207. In some embodiments, the one or more processors 207 can control the identification system 217. In other embodiments, the identification system 217 can operate independently, delivering information gleaned from detecting multi-modal social cues, emotional states, moods, and other contextual information to the one or more processors 207. In one or more embodiments, the one or more processors 207 are configured to perform the operations of the identification system 217.

Other components 221 operable with the one or more processors 207 can include output components such as video, audio, and/or mechanical outputs. For example, the output components may include a video output component or auxiliary devices including a cathode ray tube, liquid crystal display, plasma display, incandescent light, fluorescent light, front or rear projection display, and light emitting diode indicator. Other examples of output components include audio output components such as a loudspeaker disposed behind a speaker port or other alarms and/or buzzers and/or a mechanical output component such as vibrating or motion-based mechanisms.

The other components 221 can also include proximity sensors. The proximity sensors fall in to one of two camps: active proximity sensors and "passive" proximity sensors. Either the proximity detector components or the proximity sensor components can be generally used for gesture control and other user interface protocols.

The other components 221 can optionally include a barometer operable to sense changes in air pressure due to elevation changes or differing pressures of the electronic device 200. The other components 221 can also optionally include an environmental sensor 220 such as a light sensor that detects changes in optical intensity, color, light, or shadow in the environment of an electronic device. This can be used to make inferences about context such as weather or colors, walls, fields, and so forth, or other cues. An infrared sensor can be used in conjunction with, or in place of, the light sensor. The infrared sensor can be configured to detect thermal emissions from an environment about the electronic device 200. Similarly, a temperature sensor can be configured to monitor temperature about an electronic device.

A context engine 222 can then be operable with the various sensors to detect, infer, capture, and otherwise determine persons and actions that are occurring in an environment 213 about the electronic device 200. For example, where included one embodiment of the context engine 222 determines assessed contexts and frameworks using adjustable algorithms of context assessment employing information, data, and events. These assessments may be learned through repetitive data analysis. Alternatively, a user may employ a menu or user controls via the display 201 to enter various parameters, constructs, rules, and/or paradigms that instruct or otherwise guide the context engine 222 in detecting multi-modal social cues, emotional states, moods, and other contextual information. The context engine 222 can comprise an artificial neural network or other similar technology in one or more embodiments.

It is to be understood that in both FIG. 1 and FIG. 2, the elements illustrated are provided for illustrative purposes only in accordance with embodiments of the disclosure. Neither is intended to be a complete schematic diagram of the various components required. Therefore, other electronic devices in accordance with embodiments of the disclosure may include various other components obvious to those of ordinary skill in the art having the benefit of this disclosure, but not shown in FIG. 1 or FIG. 2, or may include a combination of two or more components or a division of a particular component into two or more separate components, and still be within the scope of the present disclosure.

Figure 3:
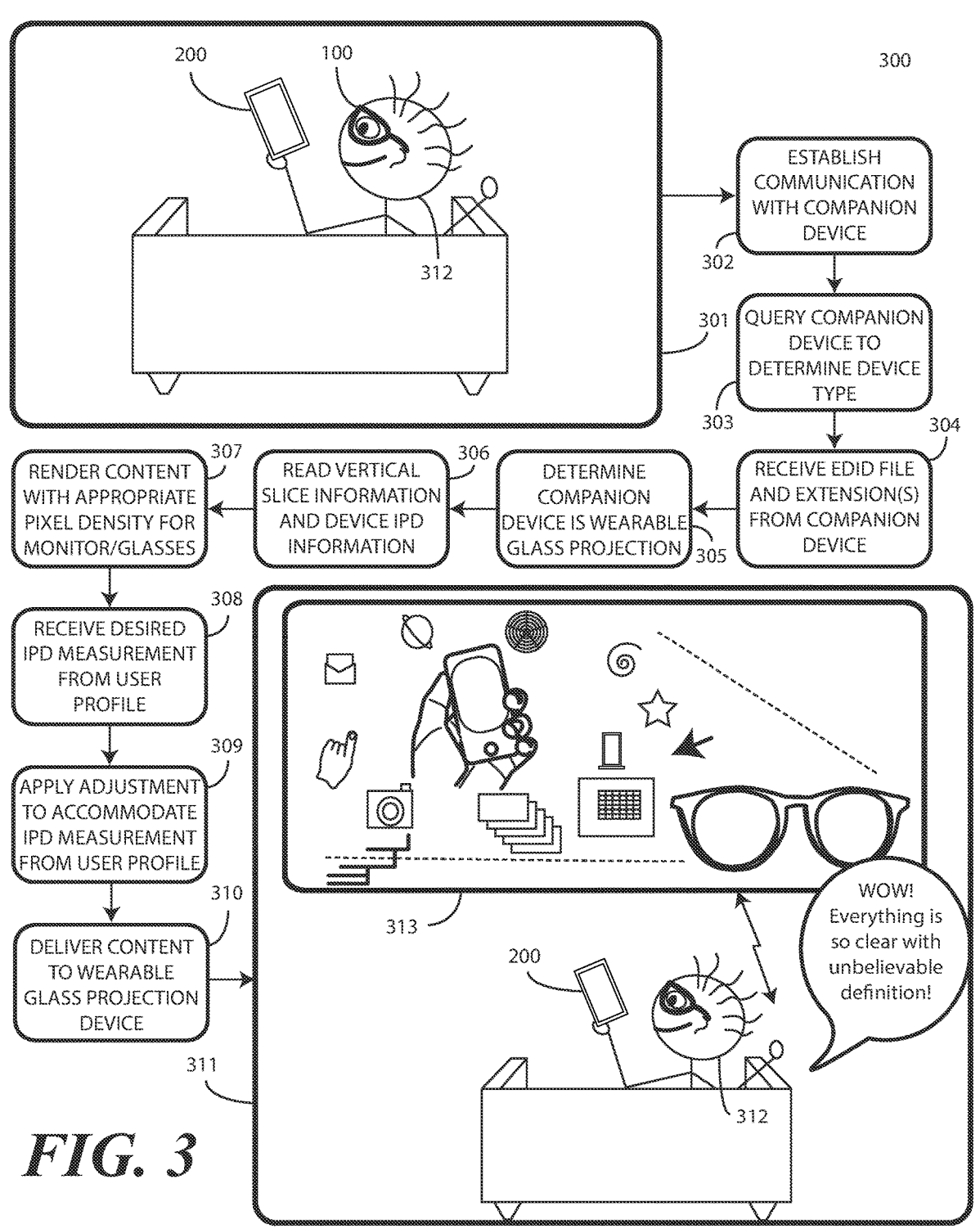
FIG. 3 illustrates one explanatory method in accordance with one or more embodiments of the disclosure.

Turning now to FIG. 3, illustrated therein is one explanatory method 300 in accordance with one or more embodiments of the disclosure. The method 300 of FIG. 3 illustrates how the companion device 100 of FIG. 1 and the electronic device 200 of FIG. 2 can be used as a system.

Beginning at step 301, the electronic device 200 is electronically in communication with the companion device 100 of FIG. 1. A user 312 is enjoying the use of the electronic device 200 while wearing the companion device 100 and sitting on a sofa in the comfort of his parlor.

At step 302, a communication device (209) of the electronic device 200 establishes a wireless electrical communication channel with the companion device 100. At step 302, the communication device (209) of the electronic device 200 queries the companion device 100 for a companion device type.

At step 304, in response to the query occurring at step 303, the communication device (209) of the electronic device 200 receives EDID (127) and one or more EDID extensions (128,129). In one or more embodiments, the EDID (127) comprises slice assignments for the companion device 100, while the EDID extensions (128, 129) comprise one or more of a field of view, pixel density, and/or interpupillary distance associated with the companion device 100. As will be described with more detail below with reference to FIG. 10, other information can be included in the EDID extensions (128,129) as well. Examples of this additional information include a lazy eye correction factor and a squint correction factor. Other examples of such information will be obvious to those of ordinary skill in the art having the benefit of this disclosure.

Turning briefly to FIG. 8, illustrated therein is an EDID file structure suitable for delivering EDID 127. The EDID file structure is a standardized communication protocol that allows a display to inform a source as to the operating capabilities it possesses. Using the EDID file structure, a companion device can inform a source device regarding operating characteristics such as native resolution, display size, aspect ratio, color definition, and other supported features. The EDID file structure can even identify the manufacturer and serial number of the content presentation companion device. The manufacturer and serial number are examples of product identification codes.

Communication of the EDID file structure allows a source device to configure the content it delivers to the content presentation companion device without the user having to manually configure the same. Additionally, the EDID file structure reduces the chance for the content being transmitted incorrectly from the source device to the content presentation companion device. Developed by the Video Electronic Standards Association (VESA), the EDID file structure allows for far more information to be delivered from a content presentation companion device to a source device than, for example, having dedicated pins attempt to carry information using binary signals.

The EDID file structure defines a 128-byte data structure that includes manufacturer and operation-related data. As shown in FIG., this information includes a vendor/product identification block, an EDID structure version and revision, basic display parameters and features, color characteristics, established timings, standard timing information, and detailed timing descriptions.

As shown in this illustrative embodiment, the EDID 127 includes horizontal and vertical slice assignments 802 for content rendering. These horizontal and vertical slice assignments 802, where populated, inform an electronic device (200) that a companion device (100) requires stereo projection. When a companion device (100) is an augmented reality companion device or virtual reality companion device, its projector (122) will frequently support a three-dimensional/stereo mode of operation. Accordingly, populating the horizontal and vertical slice assignments 802 describes the stereo projection arrangement to the electronic device (200) so that it can render content frames appropriately.

Also relevant to embodiments of the disclosure, the EDID file structure also allows for an extension flag 801. The extension flag 801, when set, indicates that an extension, which is an additional 128-byte block of data, will be included with the EDID file structure to describe increased capabilities. Such an EDID extension is used in accordance with one or more embodiments of the disclosure. When combined the logic described, the combined EDID file structure and EDID extension data can be used to determine if a companion device is a monitor, a projector, or a wearable glass projection device.

Turning now to FIG. 9, illustrated therein is one explanatory extension 128 of EDID configured in accordance with one or more embodiments of the disclosure. As shown, the extension 128 of the EDID includes a payload field 901 comprising a field of view or pixel density metric.

Where the companion device (100) is an augmented reality device, the payload field 901 comprises an augmented reality content rendering parameter. Similarly, where the companion device (100) comprises a virtual reality device, the payload field 901 comprises a virtual reality content rendering parameter.

In one or more embodiments, the payload field 901 comprises a field of view of an augmented reality presentation device or virtual reality presentation device. In one or more embodiments, the field of view is expressed in degrees. In other embodiments, the payload field 901 comprises a pixel density. Illustrating by example, the pixel density can be expressed in pixels per degree in one or more embodiments.

In one or more embodiments, the EDID extension 128 is configured to define advanced capabilities of the companion device (100) of FIG. 1, including identifying a metric that a source device, one example of which is the electronic device (200) of FIG. 2, can use to properly renderi content. Using the payload field 901, one or more processors (111) of the companion device (100) can write the identity of the field of view or pixel density to the EDID extension 128 and can cause the communication device (113) of the companion device (100) to transmit the EDID extension 128. In one or more embodiments, the communication device (113) transmits the EDID extension 128 in response to the communication device (113) detecting the establishment of a communication channel with a source device. This is in contrast to prior art systems where an EDID file structure will be transmitted in response to source device requests.

The use of an EDID extension 128 to transmit the identity of the field of view or pixel density associated with a wearable glass projection device advantageously allows legacy devices and new devices alike to properly render content for a wearable glass projection device. Even wearable glass projection devices that are not capable of utilizing the second generation of the EDID file structure can still identify the port to which a source device is connected simply by setting the EDID extension flag (801) in the EDID file structure and including the EDID extension 128 with the EDID file structure.

However, it should be understood that embodiments of the disclosure are not limited to solely using the EDID extension 128 in a wearable glass projection device to identify the wearable glass projection device content presentation parameter. In wearable glass projection devices that do support the second generation of the EDID file structure, rather than using the EDID extension 128, the second generation of the EDID file structure can simply be extended to include the payload field 901 comprising the wearable glass projection device content rendering parameter as well.

Thus, in other embodiments of the disclosure, one or more processors (111) of a companion device (100), in response to a communication device (113) detecting establishment of a display data channel with a source device, create a second generation of the EDID file structure comprising the wearable glass projection device content rendering parameter, be it a field of view metric or a pixel density metric. The one or more processors (111) then cause the communication device (113) to transmit the second generation of the EDID file structure comprising the wearable glass projection device content rendering parameter using the display data channel.

Turning briefly now to FIG. 10, illustrated therein is another explanatory EDID extension 129 in accordance with one or more embodiments of the disclosure. As shown, the EDID extension 129 also includes a payload field 1001 comprising a wearable glass projection device rendering parameter. Where the companion device (100) is an augmented reality device, the wearable glass projection device rendering parameter comprises an augmented reality content rendering parameter. Similarly, where the wearable glass projection device comprises a virtual reality device, the wearable glass projection device rendering parameter comprises a virtual reality content rendering parameter.

In one or more embodiments, the wearable glass projection device rendering parameter comprises an interpupillary distance 1002 associated with a physical configuration of the wearable glass projection device. Illustrating by example, in one or more embodiments the interpupillary distance 1002 can be defined by positions of lenses within the wearable glass projection device.

In one or more embodiments, the interpupillary distance 1002 is expressed as a distance measurement. In other embodiments, the interpupillary distance is expressed as a default measurement combined with an adjustment measurement. In one or more embodiments, this adjustment measurement can be provided on a per-lens basis.

The payload field 1001 of the EDID extension 129 can comprise other information 1003 as well. Illustrating by example, in one or more embodiments the other information 1003 comprises a lazy eye correction factor. In still other embodiments, the other information 1003 comprises a squint correction factor. Other examples of optical correction factors will be obvious to those of ordinary skill in the art having the benefit of this disclosure.

As noted above, in one or more embodiments the EDID extension 129 is configured to define advanced capabilities of the companion device (100) of FIG. 1, including identifying a metric that a source device can use to properly render content. Using the payload field 1001, one or more processors (111) of the companion device (100) can write an indication of the interpupillary distance 1002 and/or other information, examples of which include the lazy eye correction factor and/or squint correction factor, alone or in combination, to the payload field 1001 of the EDID extension 129. The one or more processors (111) and can cause the communication device (113) of the companion device (100) to transmit the EDID extension 129.

As before, in one or more embodiments the communication device (113) transmits the EDID extension 129 in response to the communication device (113) detecting the establishment of the display data channel with a source device. The use of an EDID extension 129 to transmit the interpupillary distance 1002 (and/or lazy eye correction factor or squint correction factor) advantageously allows legacy devices and new devices alike to properly render content for a wearable glass projection device. Even wearable glass projection devices that are not capable of utilizing the second generation of the EDID file structure can still identify the port to which a source device is connected simply by setting the EDID extension flag (801) in the EDID file structure and including the EDID extension 129 with the EDID file structure.

As described above, in wearable glass projection devices that do support the second generation of the EDID file structure, rather than using the EDID extension 129, the second generation of the EDID file structure can simply be extended to include the payload field 1001 comprising the wearable glass projection device content rendering parameter as well.

Turning now back to FIG. 3, at step 305 the one or more processors (207) of the electronic device 200 determine what type of companion device 100 is in communication with the communication device (209) of the electronic device 200. Techniques for doing this have been previously described. In this illustrative example, since the companion device 100 is an augmented reality companion device, step 305 comprises determining that the companion device 100 consists of a wearable glass projection device due to the fact that one or more of the field of view, the pixel density, and/or the interpupillary distance extracted from the EDID extensions (128,129) has a non-zero value. Said differently, in one or more embodiments step 305 comprises determining that the companion device 100 is a wearable glass projection device by extracting a display size having a zero value from the EDID (127) and one or more of a field of view, pixel density, and/or an interpupillary distance having non-zero values from the EDID extensions (128,129).

At step 306, the one or more processors (207) of the electronic device 200 extract slice assignments for each lens (104,105) of the companion device from the EDID (127). Step 306 can also comprise extracting the field of view or pixel density and the interpupillary distance from the EDID extensions (128,129) as well. At step 307, the one or more processors (207) render content in accordance with the slice assignments and the one or more of the field of view, pixel density, and/or the interpupillary distance.

Embodiments of the disclosure contemplate that the user 312 may have a preferred interpupillary distance that differs from that written to the EDID extension (129). The user 312 may store this user-preferred interpupillary distance in the memory (208) of the electronic device as a part of the user settings. Accordingly, at optional step 308, the one or more processors (207) of the electronic device 200 are further configured to obtain a user-preferred interpupillary distance from a user profile stored in its memory (208) and then apply an adjustment to the content as a function of the user-preferred interpupillary distance at step 309. In one or more embodiments, the adjustment applied at step 309 is proportional to a difference between the interpupillary distance and the user-preferred interpupillary distance.

In one or more embodiments, the user-preferred interpupillary distance is expressed as a distance measurement. However, in other embodiments the user-preferred interpupillary distance is expressed as a default measurement combined with an adjustment measurement per lens. Other expressions for the user-preferred interpupillary distance will be obvious to those of ordinary skill in the art having the benefit of this disclosure.

The user-preferred interpupillary distance can also be stored in the EDID extension (129). Illustrating by example, the user 312 may use user controls and settings to store the user-preferred interpupillary distance in the memory (112) of the companion device 100. The one or more processors (111) of the companion device 100 can then write the user-preferred interpupillary distance to the EDID extension (129). Where this is the case, step 308 can comprise extracting the user-preferred interpupillary distance from the EDID extension (129), while step 309 can further comprise storing the adjustment made in the memory (208) of the electronic device 200.

At step 310, the one or more processors (207) of the electronic device 200 cause the communication device (209) to transmit the rendered content to the companion device 100. At step 311, the user 312 is viewing rendered content 313 generated by the electronic device 200 and delivered to companion device 100. In this example, the rendered content 313 is rendered augmented reality content generated by the electronic device 200 and delivered to companion device 100.

As shown, the one or more processors (207) of the electronic device 200 have rendered content in accordance with the slice assignments from the EDID (127), the field of view or pixel density defined by the non-zero value found in the extension (128) of the EDID (127), and the interpupillary distance found in the other extension (129) of the EDID (127) to create rendered augmented reality content. The one or more processors (207) have also caused the communication device (209) to transmit the rendered augmented reality content to companion device 100 so that the user 312 can see the same.

In this example, the rendered augmented reality content defines an augmented reality environment. Within the augmented reality environment are presented a plurality of virtual elements. Each virtual element represents an application, widget, button, control, or other user actuation target the user 312 may select to launch corresponding applications, control hardware, and/or explore other portions of the augmented reality environment.

As shown in FIG. 3, the carousel presentation defines a ring at least partially encircling the view of electronic device 200. In one or more embodiments, the carousel presentation causes the augmented reality images defining each virtual element to encircle the view of electronic device 200. However, other configurations for the carousel presentation can occur as well. Illustrating by example, the carousel presentation could cause the augmented reality images defining each virtual element to define a square about the view of electronic device 200. Alternatively, the carousel presentation may be omitted, with the augmented reality images defining each virtual element being presented above, to the side, or below the view of the electronic device 200.

To this point, the illustrative wearable glass projection device has been an augmented reality companion device. However, embodiments are not so limited. Indeed, the slice assignments, field of view and/or pixel density metric found in the extension of the EDID, and/or interpupillary distance found in the other EDID extension can be used to render content for a virtual reality companion device as well. Turning now to FIG. 4, illustrated therein is one such virtual reality companion device.

While the companion device (100) of FIG. 1 was an augmented reality companion device, the companion device 400 of FIG. 4 is a "virtual" reality companion device. As with the augmented reality companion device of FIG. 1, the virtual reality companion device of FIG. 4 is configured as a headwear device that can be worn by a user.

In this illustrative embodiment, the companion device 400 includes a head receiver 401. The head receiver 401 is to receive a user's head. When the user desires to don the companion device 400, they place their head into the head receiver 401. The head receiver 401 can be adjustable to accommodate different sizes of heads. While the head receiver 401 is shown illustratively as a headband and overhead strap combination, it can take other forms as well, including structural shapes such as a cap, hat, helmet, or other head-covering device.

The companion device 400 also includes a shield 402 to block light from entering a virtual reality cabin positioned around the eyes of a wearer. In one or more embodiments, a virtual reality display is positioned behind this shield 402. In one embodiment, the shield 402 is manufactured from an opaque material, such as an opaque thermoplastic material.

In this illustrative embodiment, the shield 402 is coupled directly to the head receiver 401. However, other configurations will be obvious to those of ordinary skill in the art having the benefit of this disclosure. Illustrating by example, the shield 402 can be pivotally coupled to the head receiver 401 such that it can be moved between a first position relative to the head receiver 401 and a second position that is angularly displaced about the head receiver 401 relative to the first position. In still other embodiments, the shield 402 can be coupled to the head receiver 401 by way of a track. Other configurations and coupling schemes will be obvious to those of ordinary skill in the art having the benefit of this disclosure.

In one or more embodiments, a holographic optical element 403 is positioned within the virtual reality cabin positioned around the user's eyes. In one or more embodiments, the holographic optical element 403 is translucent such that ambient light can pass therethrough. The holographic optical element 403 can be any of a lens, filter, beam splitter, diffraction grating, or other device capable of reflecting light received along the interior of the virtual reality cabin to create holographic images. In one illustrative embodiment, the holographic optical element 403 comprises a pellucid holographic lens that is either integral to, or coupled to, the shield 402. Other examples of holographic optical elements will be obvious to those of ordinary skill in the art having the benefit of this disclosure.

Electronic components, many of which were described with reference to the block diagram schematic (125) of FIG. 1, can be integrated into companion device 400. Accordingly, in such embodiments the companion device 400 can include a display and corresponding electronics or alternatively a pair of displays, e.g., a left display and a right display. The display can optionally include a projector as previously described. Where a single display is used, it can of course present multiple images to the user at the same time (one for each eye). To provide a richer virtual reality experience, different information or content can be delivered to each of the user's eyes.

In one or more embodiments, the virtual reality cabin also includes one or more optical lenses situated therein. In one or more embodiments, the one or more optical lenses can bend light to make it easier for the user's eyes to see. Additionally, where multiple images are presented to the user at the same time, the one or more optical lenses can help segregate this content so that the proper content reaches the proper eye without interference from content intended for the other eye. In one embodiment, the one or more optical lenses comprise Fresnel lenses. In another embodiment, the one or more optical lenses comprise hybrid Fresnel lenses. Other types of lenses will be obvious to those of ordinary skill in the art having the benefit of this disclosure.

In one or more embodiments, a virtual reality cabin perimeter material 404 extends distally from the shield 402 to prevent ambient light from passing to the eyes of a user. This material works to ensure that the minimum quantity of exterior light reaches the user's eyes when operating as a virtual reality headset. The material can also work to improve the user experience by reducing noise introduced by ambient light interfering with the images presented by the display of the companion device 400. Moreover, the display of the companion device 400 can operate at a lower brightness, thereby conserving power when the material is in place. The material can optionally be detachable for cleaning or other operations.

The companion device 400 can optionally include integrated electronics as well. Accordingly, the head receiver 401 or another part of the companion device 400 can comprise one or more electrical components. Some of these electrical components were described above in FIG. 1. It will be clear to those of ordinary skill in the art having the benefit of this disclosure that the electrical components and associated modules can be used in different combinations, with some components and modules included and others omitted. Components or modules can be included or excluded based upon need or application.

The electronic components can include one or more processors (111). The one or more processors (111) can be operable with a memory (112). The one or more processors (111), which may be any of one or more microprocessors, programmable logic, application specific integrated circuit device, or other similar device, are capable of executing program instructions and methods. The program instructions and methods may be stored either on-board in the one or more processors (111), or in the memory (112), or in other computer readable media coupled to the one or more processors (111).

In one or more embodiments, the companion device 400 also includes an optional wireless communication device (113). Where included, the wireless communication device (113) is operable with the one or more processors (111) and is used to facilitate electronic communication with one or more electronic devices or servers or other communication devices across a network. Note that it is possible to combine the one or more processors (111), the memory (112), and the wireless communication device (113) into a single device, or alternatively into devices having fewer parts while retaining the functionality of the constituent parts.

A battery or other energy storage device can be included to provide power for the various components of the companion device 400. Again, it will be obvious to those of ordinary skill in the art having the benefit of this disclosure that other energy storage devices can be used instead of the battery, including a micro fuel cell or an electrochemical capacitor. The battery can include a lithium-ion cell or a nickel metal hydride cell, such cells having sufficient energy capacity, wide operating temperature range, large number of charging cycles, and long useful life. The battery may also include overvoltage and overcurrent protection and charging circuitry. In one embodiment, the battery comprises a small, lithium polymer cell.

Other components (116) can be optionally included in the companion device 400 as well. For example, in one embodiment one or more microphones can be included as audio capture devices. These audio capture devices can be operable with the one or more processors (111) to receive voice input. Additionally, in one or more embodiments the audio capture device can capture ambient audio noise and cancel it out. In one or more embodiments, the audio capture device can record audio to the memory (112) for transmission through the wireless communication device (113) to a server complex across a network.

The other components (116) can also include a motion generation device for providing haptic notifications or vibration notifications to a user. For example, a piezoelectric transducer, rotational motor, or other electromechanical device can be configured to impart a force or vibration upon the head receiver 401. The motion generation device can provide a thump, bump, vibration, or other physical sensation to the user. The one or more processors (111) can be configured to actuate the motion generation device to deliver a tactile or vibration output alone or in combination with other outputs such as audible outputs.

Similarly, in one or more embodiments the eyewear can include a video capture device such as an imager. In one or more embodiments, the video capture device can function as a to detect changes in optical intensity, color, light, or shadow in the near vicinity of the companion device 400. Other optional components include a global positioning system device for determining where the companion device 400 is located. The global positioning system device can communicate with a constellation of earth orbiting satellites or a network of terrestrial base stations to determine an approximate location. While a global positioning system device is one example of a location determination module, it will be clear to those of ordinary skill in the art having the benefit of this disclosure that other location determination devices, such as electronic compasses or gyroscopes, could be used as well.

An optional user interface 405 can be included. The user interface 405 can be used, for example, to activate the circuit components or turn them OFF and so forth. The user interface 405, where included, can be operable with the one or more processors (111) to deliver information to, and receive information from, a user. The user interface 405 can include a rocker switches, slider pad, button, touch-sensitive surface, or other controls, and optionally a voice command interface. These various components can be integrated together.

In one or more embodiments, an audio output device (120), such as a loudspeaker or other transducer, can deliver audio output to a user. For example, piezoelectric transducers can be operably disposed within the head receiver. Actuation of the piezoelectric transducers can cause the same to vibrate, thereby emitting acoustic output. More traditional audio output devices (117), such as loudspeakers, can be used as well.

Sensor circuits of the companion device 400 can also include motion detectors, such as one or more accelerometers, gyroscopes, magnetometers, and/or inertial motion units. For example, an accelerometer may be used to show vertical orientation, constant tilt and/or whether the companion device 400 is stationary. A gyroscope can be used in a similar fashion.

The motion detectors can also be used to determine the spatial orientation of the companion device 400 as well in three-dimensional space by detecting a gravitational direction. In addition to, or instead of, an accelerometer and/or gyroscope, an electronic compass can be included to detect the spatial orientation of the companion device 400 relative to the earth's magnetic field. Similarly, the gyroscope can be included to detect rotational motion of the companion device 400 in three-dimensional space.

The companion device 400 of FIG. 4 can operate as a stand-alone electronic device in one or more embodiments, such as when it includes a display and other corresponding electronic components as noted above. However, in other embodiments, the companion device 400 can operate in tandem with a portable electronic device, such as a smartphone or computer, to form a combined headwear/eyewear system.

The distinction between the companion device (100) of FIG. 1 and the companion device 400 of FIG. 4 is that the companion device 400 of FIG. 4 presents images to a user's eyes solely using components of the companion device 400 and without the addition of light from the physical environment. However, the components of the companion device 400 still have a field of view or pixel density associated therewith. Consequently an electronic device in communication with the companion device 400 can render content using the slice assignments, the field of view or pixel density, and/or the interpupillary distance as previously described.

Turning now to FIG. 5, illustrated therein is one explanatory method 500 in accordance with one or more embodiments of the disclosure. The method 500 of FIG. 5 allows an electronic device comprising a wireless communication device and one or more processors operable with the wireless communication device to identify a companion device electronically in communication with the wireless communication device as being one of a monitor, a projector, or a wearable glass projection device. One or more processors of the electronic device can identify a companion device electronically in communication with the wireless communication device as being a wearable glass projection device when a received EDID includes a display size having a zero value and an associated EDID extension has non-zero values for view or pixel density and interpupillary distance.

When the wearable glass projection device comprises augmented reality glasses, the method 500 facilitates the rendering of augmented reality content with a number of pixels per degree defined by the non-zero field of view and with defines slice assignments and an associated interpupillary distance to create rendered augmented reality content.

Beginning at step 501, an electronic device establishes, with a communication device, an electrical communication channel with a companion device. The companion device could be a monitor, a projector, or a wearable glass projection device 507, examples of which include augmented reality glasses 508 and virtual reality goggles 509.

At step 502, the method 500 queries, using the communication device, the companion device for a companion device type. At step 503, the method 500 receives, with the communication device, EDID. In one or more embodiments, the EDID includes one or more EDID extensions. In one or more embodiments, the one or more EDID extensions comprise one or more of a field of view or a pixel density and/or an interpupillary distance, while the EDID includes slice assignments.

At decision 504, the method 500 determines, using one or more processors of an electronic device, whether the companion device is a wearable glass projection device 507 or another type of companion device. Decision 504 can comprise determining whether the display size included with the EDID is a non-zero value. Where it is, step 506 determines that the companion device is the monitor. Content can then be rendered in accordance with the display size.

Decision 504 can also determine whether the display size of the EDID and the field of view or pixel density and/or the interpupillary distance of the EDID extensions are zero. Where they are, step 506 determines that the companion device is a projector. Content can then be rendered in accordance with a default projector parameter.

Decision 504 can also comprises determining whether the display size of the EDID is zero and the field of view or pixel density and/or interpupillary distance of the EDID extensions are non-zero values. Where this is the case, step 505 comprises determining that the companion device is a wearable glass projection device 507. Content can then be rendered, with one or more processors, in accordance with the slice assignments of the EDID and field of view or pixel density and/or interpupillary distance extracted from the EDID extensions. This rendering can be done regardless of whether the wearable glass projection device 507 is an augmented reality companion device or a virtual reality companion device in one or more embodiments.

When decision 504 fails to identify a monitor, projector, or wearable glass projection device 507, step 506 determines that the companion device is an audio only device.

The method 500 facilitates perfectly rendered content to be delivered to a wearable glass projection device for the enjoyment thereof by a user.

Turning now to FIG. 6, illustrated therein is another method 600 in accordance with one or more embodiments of the disclosure. As noted above, additional data beyond slice assignments, field of view or pixel density, and/or interpupillary distance can be used to adjust the rendering of content to personalize it for a user's preferences. The method 600 of FIG. 6 illustrates one technique for doing this. Others will be obvious to those of ordinary skill in the art having the benefit of this disclosure.

Beginning at step 601, the method 600 determines that a companion device in communication with an electronic device is a wearable glass projection device. This can be done in a variety of ways.

In one or more embodiments, step 601 comprises determining that the companion device is a wearable glass projection device by extracting a display size having a zero value from EDID and one or more of a field of view, pixel density, and/or interpupillary distance having a non-zero value from one or more extensions of the EDID. In other embodiments, step 601 comprises determining that the companion device is a wearable glass projection device when one or more of the field of view, the pixel density, and/or the interpupillary distance has a non-zero value. Other methods were described above. Still others will be obvious to those of ordinary skill in the art having the benefit of this disclosure.

At step 602, EDID is received from the companion device. In one or more embodiments, one or more EDID extensions are received with the EDID. In one or more embodiments, the one or more EDID extension define a field of view or pixel density for the companion device and an interpupillary distance for lenses of the companion device.

At step 603, slice assignments are extracted from the EDID. A field of view or pixel density is extracted from the EDID extensions. An interpupillary distance defined by lenses of the companion device can be extracted at step 603 as well. Step 604 comprises rendering content in accordance with the slice assignments, field of view or pixel density, and/or interpupillary distance.

Step 605 comprises obtaining a user-preferred interpupillary distance from a user profile stored in a non-transient memory. Decision 606 comprises determining whether the interpupillary distance from the EDID extension extracted at step 603 and the user-preferred interpupillary distance obtained at step 605 match. Where they do, the method 600 proceeds to step 608. Otherwise, the method 600 proceeds to step 607.

In one or more embodiments, step 607 comprises applying an adjustment to the content as a function of the user-preferred interpupillary distance. In one or more embodiments, step 607 comprises applying an adjustment using a default measurement combined with an adjustment measurement for each lens of the companion device. In other embodiments, step 607 comprises applying an adjustment to the content using a difference between the interpupillary distance and the user-preferred interpupillary distance. In one or more embodiments, step 607 also comprises storing the adjustment in the non-volatile memory.

At step 608, the method determines whether other adjustments need to be made to the rendered content. Illustrating by example, in one or more embodiments step 608 comprises determining, from the user profile stored in the non-transient memory, whether the user profile comprises a lazy eye correction factor. Where the user profile comprises the lazy eye correction factor, optional step 609 comprises applying another adjustment to the content as a function of the lazy eye correction factor. In one or more embodiments, the adjustment applied at step 609 comprises an angle of projection correction to compensate for the lazy eye.

In other embodiments, step 608 comprises determining, from the user profile stored in the non-transient memory, whether the user profile comprises a squint correction factor. Where the user profile comprises the squint correction factor, optional step 609 comprises applying another adjustment to the content as a function of the squint correction factor. For people with lots of optical issues, the lazy eye correction and squint correction can be applied at step 609. Accordingly, in one or more embodiments step 607 and 608 can, in one or more embodiments, comprise applying a rendering adjustment to the content as a function of optical data associated with a user of an electronic device stored in a non-transient memory. The rendered content can then be delivered to the companion device at step 610.

Figure 7:
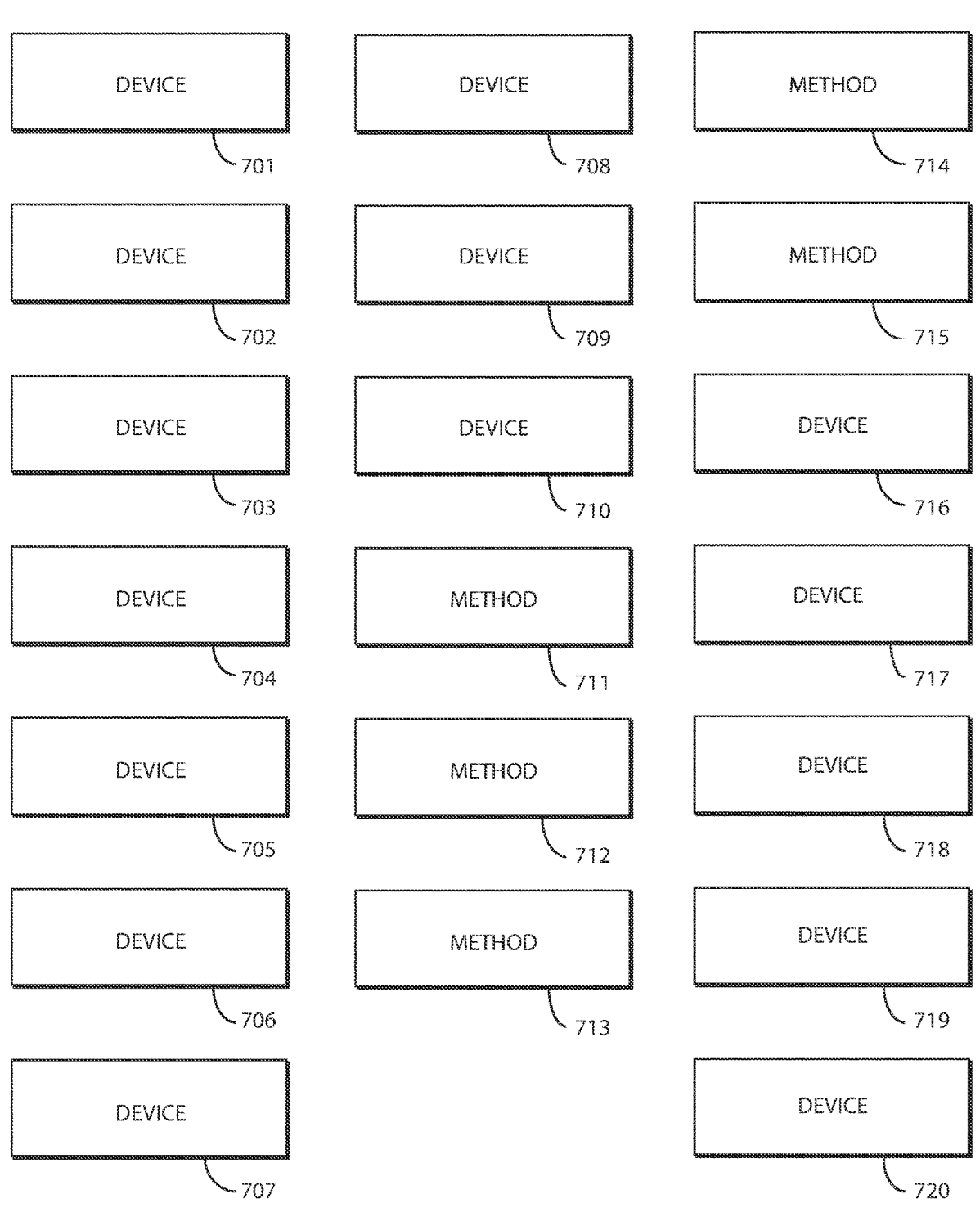
FIG. 7 illustrates various embodiments of the disclosure.

Turning now to FIG. 7, illustrated therein are various embodiments of the disclosure. The embodiments of FIG. 7 are shown as labeled boxes in FIG. 7 due to the fact that the individual components of these embodiments have been illustrated in detail in FIGS. 1-6, which precede FIG. 7. Accordingly, since these items have previously been illustrated and described, their repeated illustration is no longer essential for a proper understanding of these embodiments. Thus, the embodiments are shown as labeled boxes.

At 701, an electronic device comprises a communication device, a non-transient memory, and one or more processors operable with the communication device and the non-transient memory. At 701, the one or more processors are configured to cause, in response to the communication device detecting establishment of an electrical communication channel with a companion device, the communication device to query the companion device to determine a companion device type, and determine, in response to the communication device receiving EDID and one or more extensions of the EDID in response to the query, that the companion device is a wearable glass projection device by extracting a display size having a zero value from the EDID and one or more of a field of view, pixel density, and/or an interpupillary distance having a non-zero value from the one or more extensions of the EDID.

At 701, the one or more processors obtain slice assignments for each lens of the wearable glass projection device from the EDID. At 701, the one or more processors render content in accordance with the slice assignments and the one or more of the field of view, the pixel density, and/or the interpupillary distance. At 701, the one or more processors cause the communication device to transmit rendered content to the wearable glass projection device.

At 702, the one or more processors of 701 are further configured to obtain a user-preferred interpupillary distance from a user profile stored in the non-transient memory and apply an adjustment to the content as a function of the user-preferred interpupillary distance. At 703, the user-preferred interpupillary distance of 702 is expressed as a distance measurement. At 704, the user-preferred interpupillary distance of 702 is expressed as a default measurement combined with an adjustment measurement per lens.

At 705, the adjustment of 702 is proportional to a difference between the interpupillary distance and the user-preferred interpupillary distance. At 706, the one or more processors of 705 are further configured to store the adjustment in the user profile in the non-transient memory.

At 707, the one or more processors of 702 are further configured to determine, from the user profile stored in the non-transient memory, whether the user profile comprises a lazy eye correction factor and, where the user profile comprises the lazy eye correction factor, apply another adjustment to the content as a function of the lazy eye correction factor. At 708, the other adjustment of 707 defines an angle of projection correction.

At 709, the one or more processors of 702 are further configured to determine, from the user profile stored in the non-transient memory, whether the user profile comprises a squint correction factor. At 709, where the user profile comprises the squint correction factor, the one or more processors are configured to apply another adjustment to the content as a function of the squint correction factor.

At 710, when the wearable glass projection device of 701 comprises augmented reality glasses, the one or more processors are further configured to render augmented reality content in accordance and cause the communication device to transmit rendered augmented reality content to the augmented reality glasses. At 711, the pixel density of 701 is expressed in pixels per degree.

At 712, a method in an electronic device comprises establishing, with a communication device, a wireless electrical communication channel with a companion device. At 712, the method comprises querying, with the communication device, the companion device for companion device type.

At 712, the method comprises receiving, with the communication device, one or more EDID extensions comprising one or more of a field of view, a pixel density, and/or an interpupillary distance. At 712, the method comprises determining, with one or more processors operable with the communication device, that the companion device consists of a wearable glass projection device when the one or more of the field of view, the pixel density, and/or the interpupillary distance has a non-zero value.

At 712, the method comprises rendering, with the one or more processors, content for the wearable glass projection device using the one or more of the field of view, the pixel density, and/or the interpupillary distance has a non-zero value. At 712, the method comprises transmitting the content to the wearable glass projection device.

At 713, the method of 712 further comprises obtaining, by the one or more processors from a non-transient memory, a user interpupillary distance and applying, by the one or more processors, an interpupillary distance correction to the content using the user interpupillary distance. At 714, the method of 713 further comprises also obtaining, by the one or more processors from the non-transient memory, a lazy eye correction factor and applying, by the one or more processors, a lazy eye correction to the content using the lazy eye correction factor. At 715, the method of 713 further comprises also obtaining, by the one or more processors from the non-transient memory, a squint correction factor and applying, by the one or more processors, a squint correction to the content using the squint correction factor.

At 716, the wearable glass projection device of 713 comprises augmented reality glasses. At 716, the method further comprises, when one or more of the field of view, the pixel density, and/or the interpupillary distance has the non-zero value rendering, with the one or more processors, augmented reality content in accordance with one or more of the field of view, the pixel density, and/or the interpupillary distance to create rendered augmented reality content and transmitting, with the communication device, the rendered augmented reality content to the augmented reality glasses.

At 717, an electronic device comprises a wireless communication device, a non-transient memory device, and one or more processors operable with the wireless communication device and the non-transient memory device. At 717, the one or more processors identify a companion device electronically in communication with the wireless communication device as being a wearable glass projection device when a received EDID extension from the companion device includes a non-zero field of view, pixel density, and/or interpupillary distance value.

At 717, the one or more processors render content for the wearable glass projection device as a function of the non-zero field of view, pixel density, and/or interpupillary distance value, and applying a rendering adjustment to the content as a function of optical data associated with a user of the electronic device stored in the non-transient memory device.

At 718, the optical data of 717 comprises a user-preferred interpupillary distance. At 719, the optical data of 717 comprises a lazy eye correction factor. At 720, the optical data of 717 comprises a squint correction factor.

In the foregoing specification, specific embodiments of the present disclosure have been described. However, one of ordinary skill in the art appreciates that various modifications and changes can be made without departing from the scope of the present disclosure as set forth in the claims below. Thus, while preferred embodiments of the disclosure have been illustrated and described, it is clear that the disclosure is not so limited. Numerous modifications, changes, variations, substitutions, and equivalents will occur to those skilled in the art without departing from the spirit and scope of the present disclosure as defined by the following claims.

Accordingly, the specification and figures are to be regarded in an illustrative rather than a restrictive sense, and all such modifications are intended to be included within the scope of present disclosure. The benefits, advantages, solutions to problems, and any element(s) that may cause any benefit, advantage, or solution to occur or become more pronounced are not to be construed as a critical, required, or essential features or elements of any or all the claims.

What is claimed is:

1. An electronic device, comprising:
    a communication device;
    a non-transient memory; and
    one or more processors operable with the communication device and the non-transient memory;
    wherein the one or more processors are configured to:
        cause, in response to the communication device detecting establishment of an electrical communication channel with a companion device, the communication device to query the companion device to determine a companion device type;
        determine, in response to the communication device receiving extended display identification data (EDID) and one or more extensions of the EDID in response to the query, that the companion device is a wearable glass projection device by extracting a display size having a zero value from the EDID and one or more of a field of view, pixel density, and/or an interpupillary distance having a non-zero value from the one or more extensions of the EDID;
        render content in accordance with the one or more of the field of view, the pixel density, and/or the interpupillary distance; and
        cause the communication device to transmit rendered content to the wearable glass projection device.

2. The electronic device of claim 1, wherein the one or more processors are further configured to:
    obtain a user-preferred interpupillary distance from a user profile stored in the non-transient memory; and
    apply an adjustment to the content as a function of the user-preferred interpupillary distance.

3. The electronic device of claim 2, wherein the user-preferred interpupillary distance is expressed as a distance measurement.

4. The electronic device of claim 2, wherein the user-preferred interpupillary distance is expressed as a default measurement combined with an adjustment measurement per lens.

5. The electronic device of claim 2, wherein the adjustment is proportional to a difference between the interpupillary distance and the user-preferred interpupillary distance.

6. The electronic device of claim 5, wherein the one or more processors are further configured to store the adjustment in the user profile in the non-transient memory.

7. The electronic device of claim 2, wherein the one or more processors are further configured to:
    determine, from the user profile stored in the non-transient memory, whether the user profile comprises a lazy eye correction factor; and
    where the user profile comprises the lazy eye correction factor apply another adjustment to the content as a function of the lazy eye correction factor.

8. The electronic device of claim 7, wherein the another adjustment defines an angle of projection correction.

9. The electronic device of claim 2, wherein the one or more processors are further configured to:
    determine, from the user profile stored in the non-transient memory, whether the user profile comprises a squint correction factor; and
    where the user profile comprises the squint correction factor apply another adjustment to the content as a function of the squint correction factor.

10. The electronic device of claim 1, wherein when the wearable glass projection device comprises augmented reality glasses, the one or more processors are further configured to render augmented reality content in accordance and cause the communication device to transmit rendered augmented reality content to the augmented reality glasses.

11. The electronic device of claim 1, wherein the pixel density is expressed in pixels per degree.

12. A method in an electronic device, the method comprising:

establishing, with a communication device, a wireless electrical communication channel with a companion device;

querying, with the communication device, the companion device for companion device type;

receiving, with the communication device, one or more EDID extensions comprising one or more of a field of view, a pixel density, and/or an interpupillary distance;

determining, with one or more processors operable with the communication device, that the companion device consists of a wearable glass projection device when the one or more of the field of view, the pixel density, and/or the interpupillary distance has a non-zero value;

rendering, with the one or more processors, content for the wearable glass projection device using the one or more of the field of view, the pixel density, and/or the interpupillary distance has a non-zero value; and transmitting the content to the wearable glass projection device.

13. The method of claim 12, further comprising:

obtaining, by the one or more processors from a non-transient memory, a user interpupillary distance; and applying, by the one or more processors, an interpupillary distance correction to the content using the user interpupillary distance.

14. The method of claim 13, further comprising:

also obtaining, by the one or more processors from the non-transient memory, a lazy eye correction factor; and applying, by the one or more processors, a lazy eye correction to the content using the lazy eye correction factor.

15. The method of claim 13, further comprising:

also obtaining, by the one or more processors from the non-transient memory, a squint correction factor; and applying, by the one or more processors, a squint correction to the content using the squint correction factor.

16. The method of claim 13, wherein the wearable glass projection device comprises augmented reality glasses, further comprising when one or more of the field of view, the pixel density, and/or the interpupillary distance has the non-zero value:

rendering, with the one or more processors, augmented reality content in accordance with one or more of the field of view, the pixel density, and/or the interpupillary distance to create rendered augmented reality content; and transmitting, with the communication device, the rendered augmented reality content to the augmented reality glasses.

17. An electronic device, comprising:

a wireless communication device;

a non-transient memory device; and one or more processors operable with the wireless communication device and the non-transient memory device;

the one or more processors identifying a companion device electronically in communication with the wireless communication device as being a wearable glass projection device when a received EDID extension from the companion device includes a non-zero field of view, pixel density, and/or interpupillary distance value, rendering content for the wearable glass projection device as a function of the non-zero field of view, pixel density, and/or interpupillary distance value, and applying a rendering adjustment to the content as a function of optical data associated with a user of the electronic device stored in the non-transient memory device.

18. The electronic device of claim 17, wherein the optical data comprises a user-preferred interpupillary distance.

19. The electronic device of claim 17, wherein the optical data comprises a lazy eye correction factor.

20. The electronic device of claim 17, wherein the optical data comprises a squint correction factor.

* * * * *